United States Patent
Kimura et al.

(10) Patent No.: US 12,414,675 B2
(45) Date of Patent: Sep. 16, 2025

(54) IMAGE PROCESSING DEVICE, OPERATION METHOD, AND COMPUTER READABLE RECORDING MEDIUM

(71) Applicant: OLYMPUS CORPORATION, Tokyo (JP)

(72) Inventors: Mitsutaka Kimura, Tokyo (JP); Takehito Hayami, Tokyo (JP); Takashi Kono, Tokyo (JP); Yamato Kanda, Tokyo (JP); Ryoji Takami, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1081 days.

(21) Appl. No.: 16/420,492

(22) Filed: May 23, 2019

(65) Prior Publication Data

US 2019/0298159 A1    Oct. 3, 2019

Related U.S. Application Data

(63) Continuation of application No. PCT/JP2017/002726, filed on Jan. 26, 2017.

(51) Int. Cl.
*A61B 1/00*    (2006.01)
*A61B 1/04*    (2006.01)

(52) U.S. Cl.
CPC .... *A61B 1/000094* (2022.02); *A61B 1/00002* (2013.01); *A61B 1/00154* (2013.01);
(Continued)

(58) Field of Classification Search
CPC .......... A61B 1/00009; A61B 1/000094; A61B 1/00055; A61B 1/00097; A61B 1/00154;
(Continued)

(56) References Cited

U.S. PATENT DOCUMENTS 8,285,016 B2   10/2012   Tanaka
8,419,630 B2    4/2013   Kase et al.
(Continued)

FOREIGN PATENT DOCUMENTS

CN   101317749 A   12/2008
CN   101420897 A    4/2009
(Continued)

OTHER PUBLICATIONS

Chinese Office Action dated May 26, 2021 received in 201780082966.6.

*Primary Examiner* — Michael J Carey
*Assistant Examiner* — Stephen Floyd London
(74) *Attorney, Agent, or Firm* — Scully, Scott, Murphy & Presser, P.C.

(57) ABSTRACT

An image processing device includes a processor including hardware, the processor being configured to execute: estimating an operation state of a medical apparatus in a lumen of a subject based on information sequentially input from the medical apparatus, the medical apparatus including an imaging device, and an insertion portion inserted into the lumen, and the information including at least an intraluminal image obtained by the imaging device capturing an image inside the lumen; and performing processing corresponding to the operation state of the medical apparatus in the lumen based on an estimation result.

18 Claims, 25 Drawing Sheets

(52) U.S. Cl.
CPC .......... *A61B 1/041* (2013.01); *A61B 1/00055* (2013.01); *G06T 2207/30101* (2013.01)

(58) Field of Classification Search
CPC ... A61B 1/045; A61B 1/05; A61B 2034/2055; A61B 2034/2057; A61B 2034/2065; A61B 2090/062; G06T 7/248; G06T 7/70; G06T 7/74; G06T 2207/10068
See application file for complete search history.

(56) References Cited

U.S. PATENT DOCUMENTS

| | | | | |
|---|---|---|---|---|
| 2005/0010082 | A1* | 1/2005 | Nishimura | A61B 1/00147 600/145 |
| 2006/0293558 | A1* | 12/2006 | De Groen | G06T 7/0012 600/101 |
| 2008/0303898 | A1* | 12/2008 | Nishimura | G16H 40/63 348/E7.085 |
| 2009/0041320 | A1* | 2/2009 | Tanaka | A61B 1/00147 382/128 |
| 2009/0161927 | A1* | 6/2009 | Mori | A61B 6/466 382/128 |
| 2011/0166418 | A1* | 7/2011 | Aoyagi | A61B 1/00009 600/109 |
| 2011/0208000 | A1* | 8/2011 | Honda | A61B 1/0016 600/118 |
| 2011/0230712 | A1* | 9/2011 | Matsuura | A61B 1/01 600/106 |
| 2011/0275889 | A1* | 11/2011 | Kase | A61B 1/0005 600/103 |
| 2014/0081083 | A1* | 3/2014 | Morita | A61B 1/00177 600/109 |
| 2014/0303435 | A1* | 10/2014 | Taniguchi | A61B 1/00006 600/103 |
| 2015/0208947 | A1* | 7/2015 | Tojo | A61B 1/009 600/104 |
| 2015/0359419 | A1* | 12/2015 | Hane | A61B 1/07 600/117 |
| 2016/0292498 | A1* | 10/2016 | Miura | A61B 1/01 |
| 2017/0188839 | A1* | 7/2017 | Tashiro | A61B 5/0095 |
| 2023/0360221 | A1* | 11/2023 | Kamon | A61B 1/00055 |

FOREIGN PATENT DOCUMENTS

| | | |
|---|---|---|
| CN | 102469930 A | 5/2012 |
| JP | 2005348902 A * | 12/2005 |

* cited by examiner

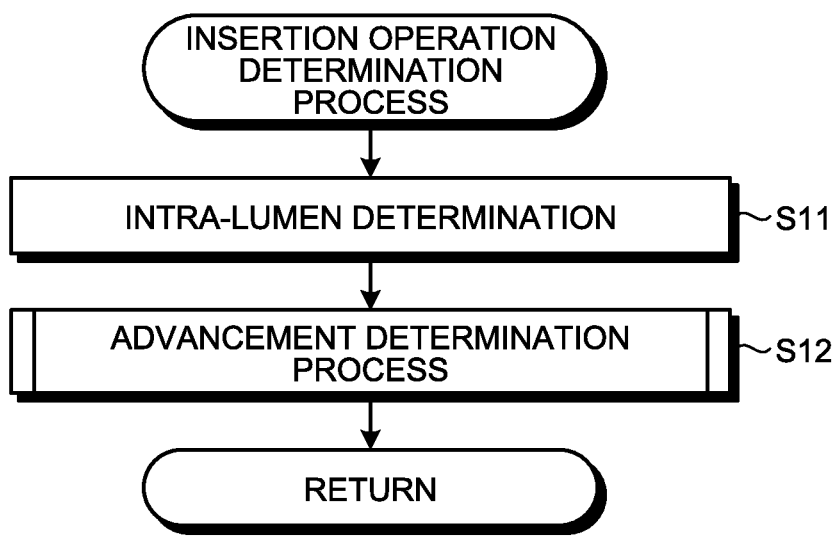
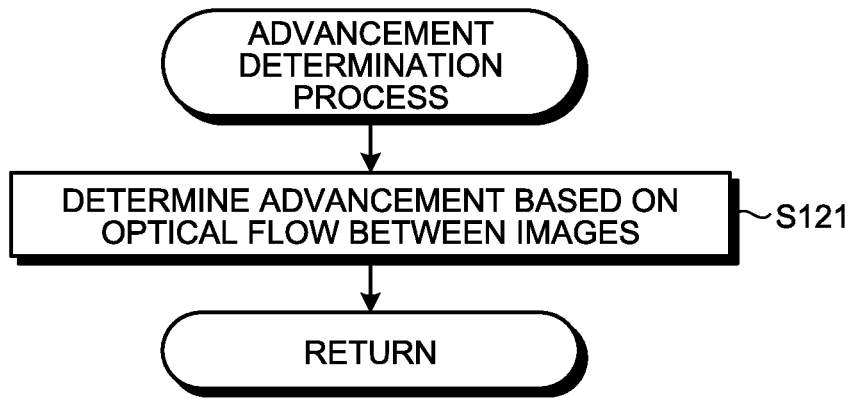

IMAGE PROCESSING DEVICE, OPERATION METHOD, AND COMPUTER READABLE RECORDING MEDIUM

CROSS REFERENCE TO RELATED APPLICATION

This application is a continuation of International Application No. PCT/JP2017/002726, filed on Jan. 26, 2017, the entire contents of which are incorporated herein by reference.

BACKGROUND

The present disclosure relates to an image processing device, an operation method, and a computer readable recording medium.

JP 2010-63589 A discloses a technique of detecting an amount of relative movement of an observed region and switching normal illumination light and special illumination light based on a detection result. In this technique, the normal illumination light and the special illumination light are emitted alternately when the detection result is equal to or smaller than a threshold, and the special illumination light only is emitted when the detection result exceeds the threshold.

SUMMARY

An image processing device according to one aspect of the present disclosure includes a processor including hardware, the processor being configured to execute: estimating an operation state of a medical apparatus in a lumen of a subject based on information sequentially input from the medical apparatus, the medical apparatus including an imaging device, and an insertion portion inserted into the lumen, and the information including at least an intraluminal image obtained by the imaging device capturing an image inside the lumen, wherein the estimating includes determining an insertion operation of the medical apparatus in the lumen by: determining whether the imaging device is inserted into the lumen; and determining whether the medical apparatus is advancing toward an observation target in the lumen, wherein the medical apparatus is determined to be advancing until a predetermined degree of matching between the intraluminal image and the observation target reaches a predetermined reference value; and performing processing corresponding to the operation state of the medical apparatus in the lumen based on an estimation result, wherein the performing includes performing processing corresponding to the insertion operation when the medical apparatus is determined to be inserted into the lumen.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 4 is a flowchart illustrating an overview of an insertion operation determination process in FIG. 3;

FIG. 5 is a flowchart illustrating an overview of an advancement determination process in FIG. 4;

DETAILED DESCRIPTION

Figure 1:
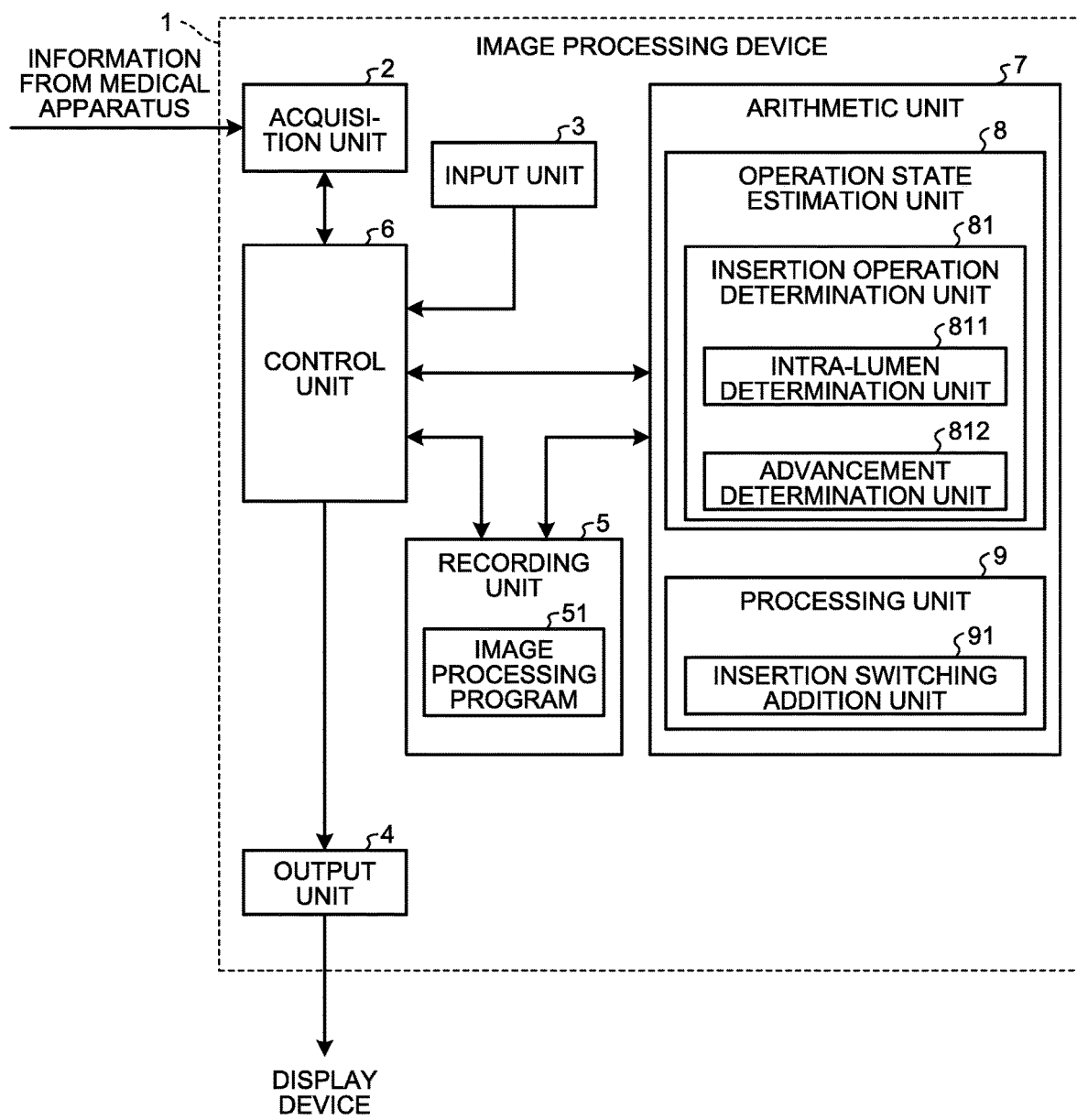
FIG. 1 is a block diagram illustrating a configuration of an image processing device according to a first embodiment.

Hereinafter, an image processing device, an operation method, and a program according to embodiments will be described with reference to the drawings. The present disclosure is not limited to these embodiments. Moreover, in the respective drawings, the same portions will be denoted by the same reference numerals.

First Embodiment

Configuration of Image Processing Device

FIG. 1 is a block diagram illustrating a configuration of an image processing device according to a first embodiment. An image processing device 1 (e.g., a processor including hardware) according to the first embodiment is a device that estimates the state of an insertion operation of a medical apparatus and performs processing according to an estimation result based on information from the medical apparatus or intraluminal images arranged in a time-series order and continuously, of the inside of the lumen of a subject by an endoscope or a capsule endoscope (hereinafter these endoscopes will be collectively referred to simply as a "medical device") including an endoscope scope such as a flexible endoscope or a rigid endoscope, as an example. Moreover, an intraluminal image is generally a color image having a pixel level (a pixel value) for wavelength components of R (red), G (green), and B (blue) at each pixel position. Moreover, a lesion region is a specific region (that is, an abnormal region) in which a lesion such as bleeding, reddening, coagulated blood, tumor, sore, ulcer, aphtha, and villus abnormality, or a portion regarded as abnormality.

Furthermore, in the following description, insertion means an operation until a distal end of a medical apparatus reaches a target position after the distal end enters into the lumen of a subject. Moreover, removal means an operation until the distal end of the medical apparatus comes out of the lumen after the distal end reaches the target position inside the lumen of a subject. Moreover, a path until the distal end reaches the target position will be referred to as advancement, and a path until the distal end comes out of the lumen of the subject from the target position will be referred to as retraction. Furthermore, the information from the medical apparatus includes operation information of an operator on the medical apparatus, information from sensors such as an acceleration sensor, a temperature sensor, and a magnetic field generation sensor provided at the distal end of the medical apparatus, and shape information related to the shape of the distal end of the medical apparatus, in addition to the intraluminal image.

The image processing device 1 illustrated in FIG. 1 includes an acquisition unit 2 that acquires information including the intraluminal image captured by the medical apparatus from the medical apparatus or an external apparatus, an input unit 3 that receives an input signal input by an operation from the outside, an output unit 4 that outputs images and various pieces of information to a display device, a recording unit 5 that records the intraluminal image acquired by the acquisition unit 2, the information from the medical apparatus, and various programs, a control unit 6 (e.g., a controller implemented by a processor including hardware) that controls an operation of the entire image processing device 1, and an arithmetic unit 7 (e.g., an arithmetic unit implemented by a processor including hardware) that switches predetermined image processing and another processing with respect to the intraluminal image. In a first embodiment, although the acquisition unit 2 acquires information including the intraluminal image from an external medical apparatus, an imaging unit having an imaging function may be provided in the image processing device 1, for example, so as to capture an intraluminal image.

The acquisition unit 2 is configured appropriately according to the aspect of a system including the medical apparatus. For example, when a portable recording medium is used for exchanging an intraluminal image with the medical apparatus, the acquisition unit 2 is configured as a reader to which the recording medium is detachably attached to read the recorded intraluminal image. Moreover, when a server that records an intraluminal image captured by the medical apparatus is used, the acquisition unit 2 is configured as a communication device or the like that can communicated with the server bidirectionally to perform data communication with the server to acquire the intraluminal image. Furthermore, the acquisition unit 2 may be configured as an interface device or the like to which the intraluminal image is input from the medical apparatus via a cable.

The input unit 3 is realized by an input device such as, for example, a keyboard, a mouse, a touch panel, and various switches and outputs the input signal received according to an operation from the outside to the control unit 6. The input unit 3 may not necessarily be a wired device but may be a radio device, for example.

The output unit 4 outputs information and images extracted by the arithmetic operation of the arithmetic unit 7 to a display device connected by wired connection or a display device connected by radio communication under the control of the control unit 6. Here, the output unit 4 may be configured using a liquid crystal or organic electro luminescence (EL) display panel or the like and may display various images including images processed by an arithmetic operation of the arithmetic unit 7 and may output a warning via sound, text, or the like.

The recording unit 5 is realized by various IC memories such as a flash memory, a read only memory (ROM), and a random access memory (RAM) and a built-in hard disk or a hard disk connected by a data communication terminal. The recording unit 5 records a program for operating the image processing device 1 and causing the image processing device 1 to execute various functions, data used during execution of the program, and the like in addition to the intraluminal image or a video acquired by the acquisition unit 2. For example, the recording unit 5 records an image processing program 51 for performing an optical flow or the like on the intraluminal image and various pieces of information used during execution of the program. Furthermore, the recording unit 5 records a template in which the feature of a lesion or the like is set in advance and a reference used for judgment of a lesion when the arithmetic unit 7 performs lesion detection or the like.

The control unit 6 is configured using a general purpose processor such as central processing unit (CPU) or a special purpose processor such as various arithmetic circuits that execute specific functions such as application specific integrated circuit (ASIC) or field programmable gate array (FPGA). When the control unit 6 is a general purpose processor, the control unit 6 reads various programs stored in the recording unit 5 and performs transmission of instructions and data to respective units of the image processing device 1 or the like to control the operation of the entire image processing device 1 in an integrated manner. Moreover, when the control unit 6 is a special purpose processor, the processor may execute various processes alone and the processor and the recording unit 5 may execute various processes in cooperation or combination with each other using various pieces of data stored in the recording unit 5.

The arithmetic unit 7 is configured using a general purpose processor such as CPU or a special purpose processor such as various arithmetic circuits that execute specific functions such as ASIC or FPGA. When the arithmetic unit 7 is a general purpose processor, the arithmetic unit 7 reads the image processing program 51 from the recording unit 5 to estimate the state of an insertion operation in the lumen, of the medical apparatus and execute processing corresponding to the estimated operation based on the acquired intraluminal image or the information from the medical apparatus. Moreover, when the arithmetic unit 7 is a special purpose processor, the processor may execute various processes alone and the processor and the recording unit 5 may execute various processes in cooperation or combination with each other using various pieces of data stored in the recording unit 5.

Detailed Configuration of Arithmetic Unit

Next, a detailed configuration of the arithmetic unit 7 will be described. The arithmetic unit 7 includes an operation state estimation unit 8 and a processing unit 9.

The operation state estimation unit 8 estimates the operation state of the medical apparatus inside the lumen based on the inflator sequentially input from the medical apparatus, acquired by the acquisition unit 2 via the control unit 6 or the recording unit 5. The operation state estimation unit 8 includes an insertion operation determination unit 81.

The insertion operation determination unit 81 determines an insertion operation inside the lumen, of the medical apparatus based on the information sequentially input from the medical apparatus, acquired by the acquisition unit 2 via the control unit 6 or the recording unit 5. The insertion operation determination unit 81 includes an intra-lumen determination unit 811 that determines whether the imaging device included in the medical apparatus is inserted into the lumen and an advancement determination unit 812 that determines whether the medical apparatus is in an advancement in the middle of an insertion operation toward an observation target.

The processing unit 9 performs a process corresponding to the operation state of the medical apparatus inside the lumen based on an estimation result obtained by the operation state estimation unit 8. The processing unit 9 includes an insertion switching addition unit 91.

When the operation state estimation unit 8 determines that an insertion operation is performed, the insertion switching addition unit 91 switches to a process corresponding to the insertion operation or adds a process.

Processing of Image Processing Device

Figure 2:
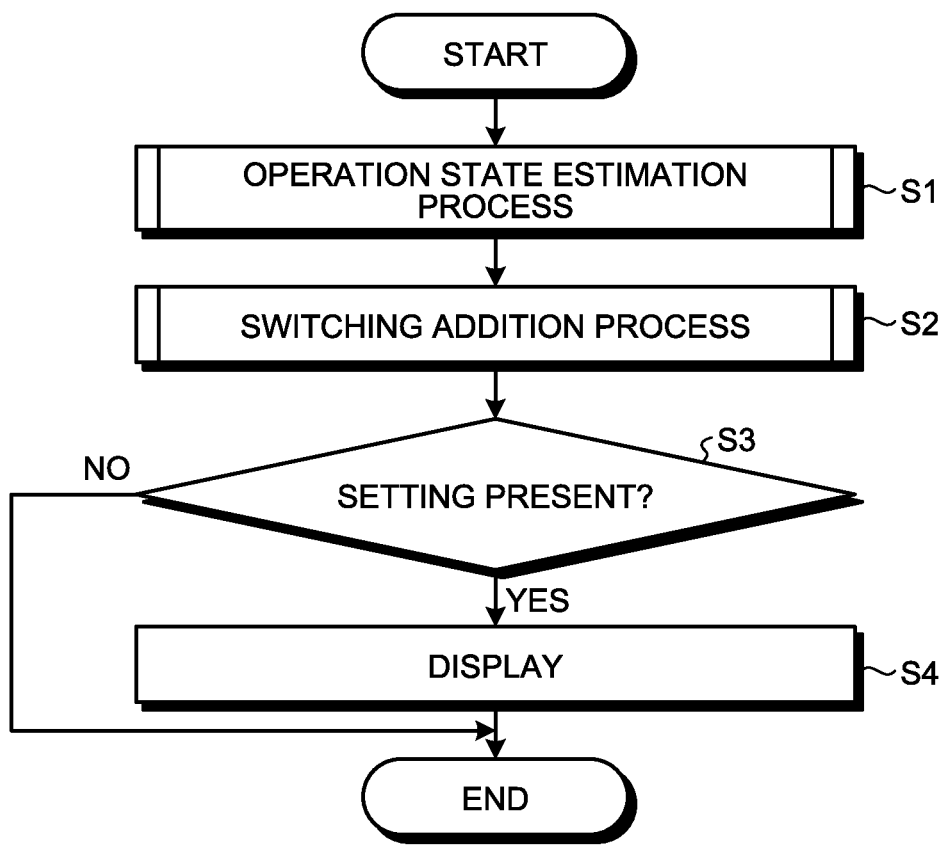
FIG. 2 is a flowchart illustrating an overview of a process executed by the image processing device according to the first embodiment.

Next, a process executed by the image processing device 1 will be described. FIG. 2 is a flowchart illustrating an overview of the process executed by the image processing device 1.

As illustrated in FIG. 2, first, the operation state estimation unit 8 executes an operation state estimation process of estimating an operation state of the medical apparatus based on the intraluminal image acquired by the acquisition unit 2 (Step S1). After Step S1 is performed, the image processing device 1 proceeds to Step S2 to be described later.

Figure 3:
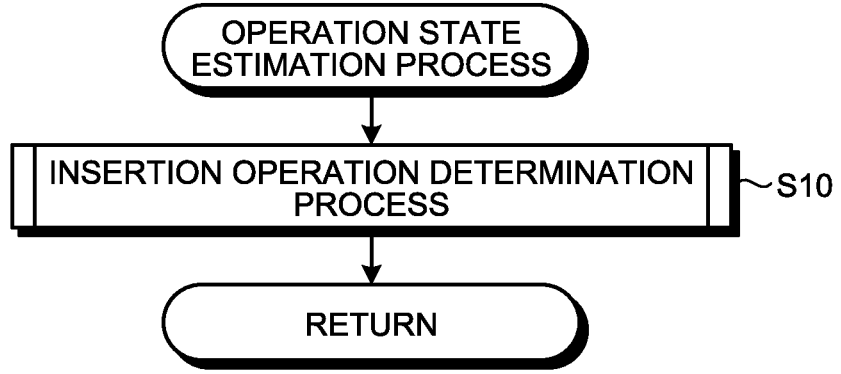
FIG. 3 is a flowchart illustrating an overview of an operation state estimation process in FIG. 2.

FIG. 3 is a flowchart illustrating an overview of an operation state estimation process of Step S1 in FIG. 2. As illustrated in FIG. 3, the insertion operation determination unit 81 executes an insertion operation determination process of determining whether the medical apparatus is inserted into the lumen based on the intraluminal image acquired by the acquisition unit 2 (Step S10). Specifically, the insertion operation determination unit 81 determines whether an insertion portion included in the medical apparatus is present inside the lumen and determines whether the medical apparatus proceeds toward a target position by performing an insertion operation based on the intraluminal image acquired by the acquisition unit 2. After Step S10 is performed, the image processing device 1 returns to a main routine of FIG. 2.

FIG. 4 is a flowchart illustrating an overview of the insertion operation determination process of Step S10 in FIG. 3. As illustrated in FIG. 4, the intra-lumen determination unit 811 determines whether the distal end of the imaging device included in the medical apparatus is present inside the lumen (Step S11). Specifically, the intra-lumen determination unit 811 determines whether the distal end of the insertion portion included in the medical apparatus is present inside the lumen by comparing the intraluminal image acquired by the acquisition unit 2 with a predetermined reference which can be identified to be inside the lumen. Naturally, the intra-lumen determination unit 811 may determine whether the distal end of the insertion portion included in the medical apparatus is present inside the lumen based on feature data of the intraluminal image, for example, in addition to the reference-based determination, and may determine whether the distal end of the insertion portion included in the medical apparatus is present inside the lumen based on a statistical value such as the tone, the brightness, and the RGB histogram of the intraluminal image.

Subsequently, the advancement determination unit 812 executes an advancement determination process of determining whether the medical apparatus is in an advancement in the middle of an insertion operation toward an observation target (Step S12). After Step S12 is performed, the image processing device 1 returns to a subroutine of the operation state estimation process in FIG. 3.

FIG. 5 is a flowchart illustrating an overview of the advancement determination process of Step S12 in FIG. 4. As illustrated in FIG. 5, the advancement determination unit 812 determines whether the medical apparatus is in an advancement based on an optical flow of two intraluminal images which are successive in time (Step S121). Specifically, the advancement determination unit 812 calculates a local motion according to an optical flow between images and estimates an advancing direction of the medical apparatus in the lumen based on the calculation result obtained by the calculation. When the medical apparatus is advancing into the lumen toward the target position, it is determined that the medical apparatus is in the advancement. Moreover, when the medical apparatus is inserted into the lumen, the medical apparatus is sometimes moved back and forth inside the lumen. Due to this, the advancement determination unit 812 may set a predetermined period and may increase the accuracy of determination on an advancement using a local motion in the predetermined period. The predetermined period may be set via the input unit 3 and an optical period may be set in advance by experiment or the like. Moreover, the advancement determination unit 812 may estimate a moving distance from the measurement result from an acceleration sensor or a motion sensor (an azimuth sensor or a gyro sensor), included in the information from the medical apparatus and may determine whether the medical apparatus is in the advancement based on the estimated moving distance. Alternatively, the advancement determination unit 812 may compare the intraluminal image with a predetermined reference image and determine whether the medical apparatus is in the advancement based on the comparison result. After Step S13 is performed, the image processing device 1 returns to the subroutine of the insertion operation determination process in FIG. 4.

Returning to FIG. 2, the description of Step S2 and the subsequent steps will be continued.

In Step S2, the processing unit 9 executes a switching addition process of performing processing corresponding to the operation state of the medical apparatus, inside the lumen based on the estimation result of the operation state estimation unit 8. After Step S2 is performed, the image processing device 1 proceeds to Step S3 to be described later.

Figure 6:
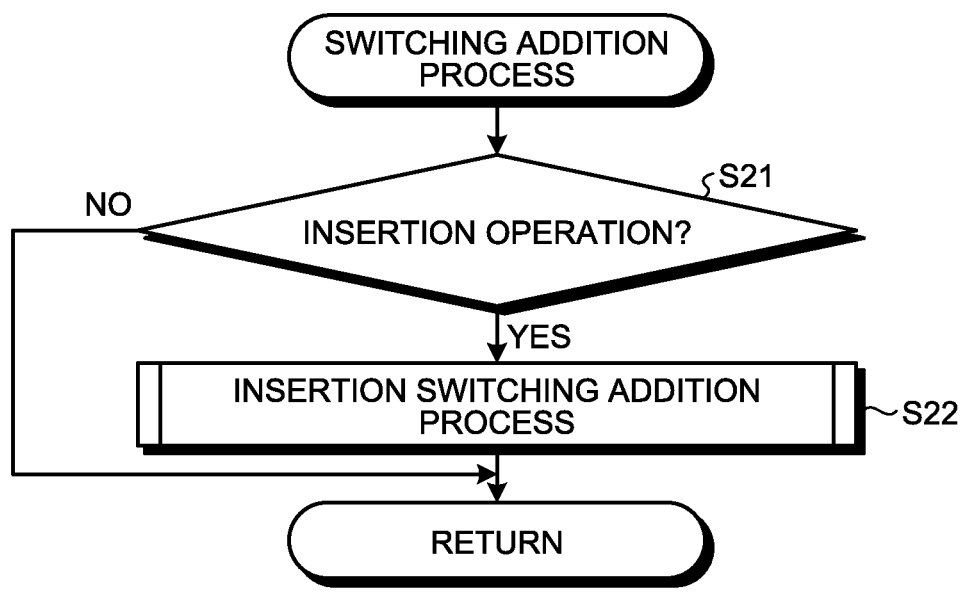
FIG. 6 is a flowchart illustrating an overview of a switching addition process in FIG. 2.

FIG. 6 is a flowchart illustrating an overview of the switching addition process of Step S2 in FIG. 2. As illustrated in FIG. 6, when the operation state estimation unit 8 estimates that the medical apparatus is performing an insertion operation inside the lumen (Step S21: Yes), the insertion switching addition unit 91 executes an insertion switching addition process of switching to processing corresponding to the insertion operation or adding a process (Step S22). After Step S22 is performed, the image processing device 1 returns to the main routine of FIG. 2. In contrast, when the operation state estimation unit 8 estimates that the medical apparatus is not performing an insertion operation inside the lumen (Step S21: No), the image processing device 1 returns to the main routine of FIG. 2.

Figure 7:
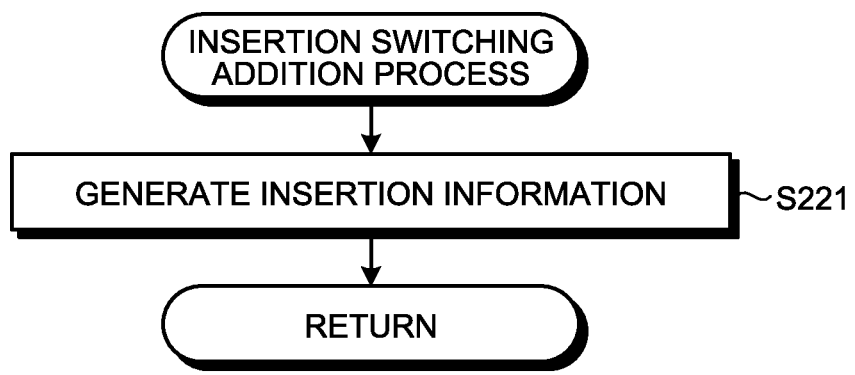
FIG. 7 is a flowchart illustrating an overview of the switching addition process in FIG. 6.

FIG. 7 is a flowchart illustrating an overview of the insertion switching addition process of Step S22 in FIG. 6. As illustrated in FIG. 7, the insertion switching addition unit 91 outputs insertion information to the output unit 4 (Step S221). Specifically, the insertion switching addition unit 91 generates information indicating that the operation state estimation unit 8 has estimated that the medical apparatus is inside the lumen or that the medical apparatus is being inserted into the lumen. After Step S221 is performed, the image processing device 1 returns to the subroutine of FIG. 6.

Returning to FIG. 2, the description of Step S3 and the subsequent steps will be continued.

Figure 8:
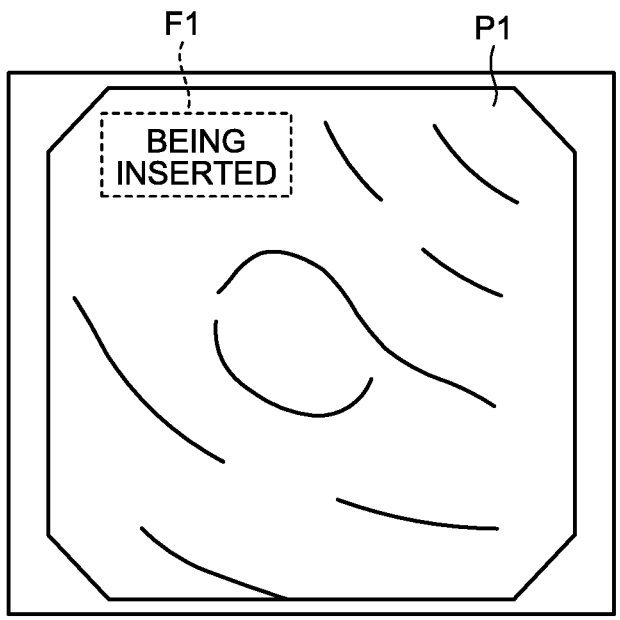
FIG. 8 is a diagram schematically illustrating an example of an image displayed on a display device in an insertion switching addition process.

In Step S3, when it is set via the input unit 3 that information is to be displayed on the display device (Step S3: Yes), the output unit 4 displays an estimation result of the operation state estimation unit 8 and a processing content of the processing unit 9 on the display device by outputting the same to the display device (Step S4). Specifically, as illustrated in FIG. 8, the output unit 4 outputs information F1 indicating that the medical apparatus is being inserted into the lumen, generated by the insertion switching addition unit 91 to the display device so that the information F1 is displayed on an intraluminal image P1 displayed by the display device. In this way, an operator can understand the present state of the medical apparatus immediately. The output unit 4 may output sound or light indicating that the medical apparatus is being inserted into the lumen instead of the information F1. After Step S4 is performed, the image processing device 1 ends this process. In contrast, when it is set via the input unit 3 that information is not to be displayed on the display device (Step S3: No), the image processing device 1 ends this process.

According to the first embodiment described above, since processing can be performed according to the operation state inside the lumen, of the medical apparatus, it is possible to assist endoscope-based examination by the operator.

First Modification of First Embodiment

Next, a first modification of the first embodiment will be described. The first modification of the first embodiment is different in terms of the advancement determination process executed by the image processing device. In the following description, an advancement determination process executed by the image processing device according to the first modification of the first embodiment will be described. The same components as those of the image processing device 1 according to the first embodiment will be denoted by the same reference numerals and the description thereof will be omitted.

Figure 9:
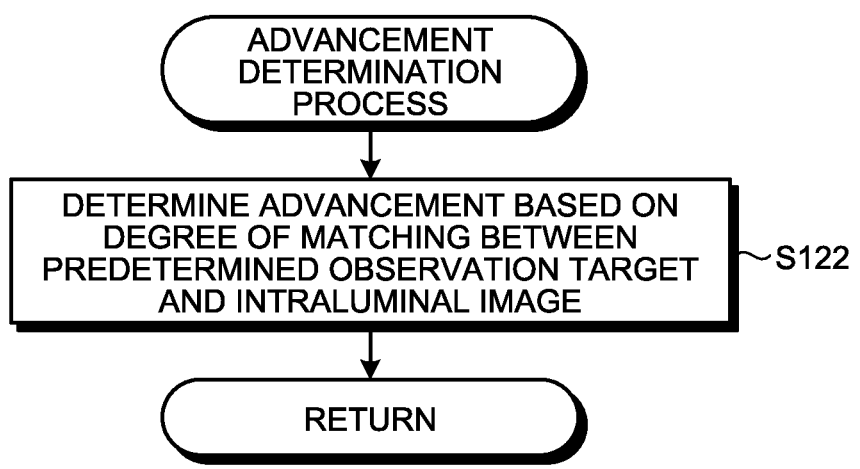
FIG. 9 is a flowchart illustrating an overview of an advancement determination process executed by an image processing device according to a first modification of the first embodiment.

FIG. 9 is a flowchart illustrating an overview of an advancement determination process executed by the image processing device according to the first modification of the first embodiment.

As illustrated in FIG. 9, the advancement determination unit 812 determines whether the medical apparatus is in an advancement in the middle of an insertion operation toward an observation target in the lumen based on the degree of matching between the intraluminal image and a predetermined observation target (Step S122). For example, when the large intestine of a subject is examined, an operator inserts the medical apparatus up to the ileocecum, and after the medical apparatus reaches the ileocecum, performs observation while removing the medical apparatus from the ileocecum. In this case, the advancement determination unit 812 sets the ileocecum as an observation target in advance and determines whether the intraluminal images sequentially captured in a time-series order by the medical apparatus are the ileocecum. The advancement determination unit 812 performs the determination until the intraluminal image matches the observation target and determines that the medical apparatus is in the advancement until an intraluminal image of which the degree of matching with respect to the observation target is equal to or larger than a predetermined threshold is captured. Moreover, the advancement determination unit 812 may determine whether the medical apparatus is in the advancement by comparing the intraluminal image and a reference image (a reference) serving as an observation target for the degree of matching. Furthermore, the advancement determination unit 812 may determine that the medical apparatus has reached the observation target when the intraluminal image does not match the observation target in a predetermined period. After Step S122 is performed, the image processing device 1 returns to the subroutine of the insertion operation determination process in FIG. 4.

According to the first modification of the first embodiment described above, since processing can be performed according to the operation state inside the lumen, of the medical apparatus, it is possible to assist endoscope-based examination by the operator.

Second Modification of First Embodiment

Next, a second modification of the first embodiment will be described. The second modification of the first embodiment is different in terms of the advancement determination process executed by the image processing device. In the following description, an advancement determination process executed by the image processing device according to the second modification of the first embodiment will be described. The same components as those of the image processing device 1 according to the first embodiment will be denoted by the same reference numerals and the description thereof will be omitted.

Figure 10:
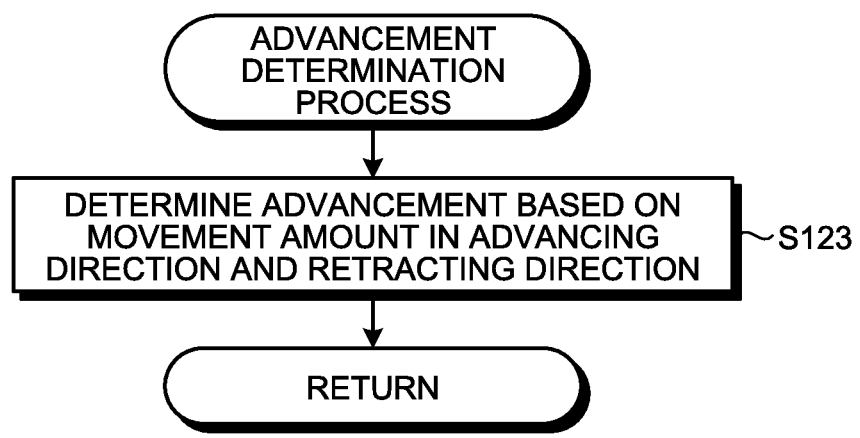
FIG. 10 is a flowchart illustrating an overview of an advancement determination process executed by an image processing device according to a second modification of the first embodiment.

FIG. 10 is a flowchart illustrating an overview of an advancement determination process executed by an image processing device according to the second modification of the first embodiment. As illustrated in FIG. 10, the advancement determination unit 812 calculates a movement amount in each of a moving direction (an insertion direction or a direction toward the observation target) and a retracting direction (a removal direction) of the medical apparatus based on a detection result detected by an acceleration sensor, included in the information of the medical apparatus, acquired by the acquisition unit 2 and determines that the medical apparatus is in the advancement when the movement amount in the advancing direction is larger than the movement amount in the retracting direction (Step S123). Here, a sensor (for example, a gyro sensor) other than the acceleration sensor may be used as long as the movement amount and the moving direction of the imaging device provided in the medical apparatus can be acquired. After Step S123 is performed, the image processing device 1 returns to the subroutine of the insertion operation determination process in FIG. 4.

According to the second modification of the first embodiment described above, since processing can be performed according to the operation state inside the lumen, of the medical apparatus, it is possible to assist endoscope-based examination by the operator.

Second Embodiment

Next, a second embodiment will be described. The second embodiment is different in terms of the configuration of the arithmetic unit 7 of the image processing device 1 according to the first embodiment. In the following description, the configuration of an image processing device according to the second embodiment will be described first, and then, the process executed by the image processing device according to the second embodiment will be described. The same components as those of the image processing device 1 according to the first embodiment will be denoted by the same reference numerals and the description thereof will be omitted.

Configuration of Image Processing Device

Figure 11:
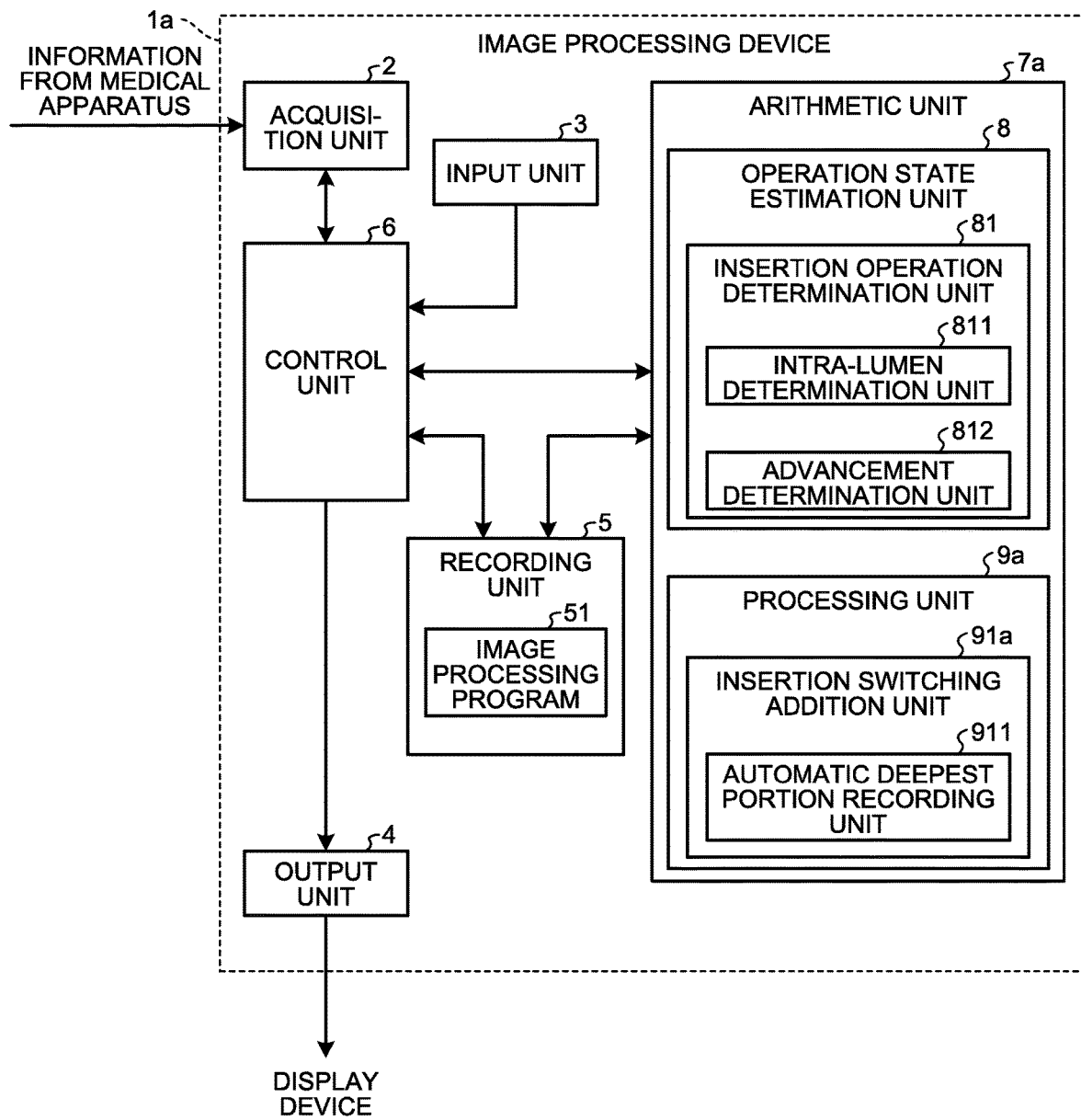
FIG. 11 is a block diagram illustrating a configuration of an image processing device according to a second embodiment.

FIG. 11 is a block diagram illustrating a configuration of an image processing device according to the second embodiment. An image processing device 1a illustrated in FIG. 11 includes an arithmetic unit 7a instead of the arithmetic unit 7 according to the first embodiment. The arithmetic unit 7a includes a processing unit 9a instead of the processing unit 9 according to the first embodiment. The processing unit 9a includes an insertion switching addition unit 91a instead of the insertion switching addition unit 91 according to the first embodiment. The insertion switching addition unit 91a includes an automatic deepest portion recording unit 911 that automatically records an intraluminal image on the recording unit 5 when the operation state estimation unit 8 determines that the intraluminal image from the medical apparatus is a deepest portion of the observation target.

Processing of Image Processing Device

Figure 12:
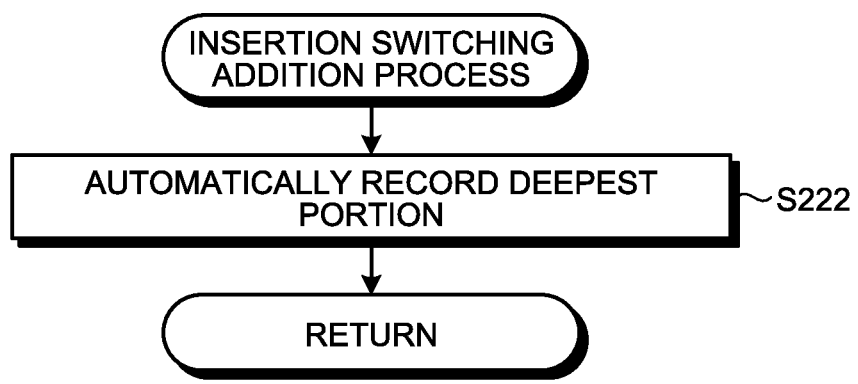
FIG. 12 is a flowchart illustrating an overview of an insertion switching addition process executed by the image processing device according to the second embodiment.

Next, the process executed by the image processing device 1a will be described. The image processing device 1a executes processing similar to that of the image processing device 1 according to the first embodiment and is different in terms of the insertion switching addition process in FIG. 7. In the following description, the insertion switching addition process executed by the image processing device 1a will be described. FIG. 12 is a flowchart illustrating an overview of the insertion switching addition process executed by the image processing device 1a.

As illustrated in FIG. 12, the automatic deepest portion recording unit 911 records an intraluminal image on the recording unit 5 automatically when the operation state estimation unit 8 determines that the intraluminal image from the medical apparatus is a deepest portion of the observation target (Step S222). For example, the automatic deepest portion recording unit 911 records an intraluminal image on the recording unit 5 automatically when the advancement determination unit 812 of the first modification of the first embodiment determines that the intraluminal image is the ileocecum at the deepest portion of the observation target. The intraluminal images recorded automatically are captured continuously by the medical apparatus and are identified as the intraluminal image acquired sequentially by the acquisition unit 2 and are recorded on the recording unit 5. Here, the reason why the intraluminal images are identified and recorded on the recording unit 5 is to verify that the operator has examined a subject. Moreover, other identified intraluminal images may be output to the outside by the output unit 4 so that the images are used as an examination report of the subject. Moreover, when the advancement determination unit 812 determines that the intraluminal image is the ileocecum at the deepest portion of the observation target, the automatic deepest portion recording unit 911 may cause the output unit 4 to output a imaging instruction signal to the imaging device of the medical apparatus, identify the intraluminal image input from the medical apparatus as another intraluminal image, and record the intraluminal image on the recording unit 5. After Step S222 is performed, the image processing device 1a returns to the subroutine of the switching addition process in FIG. 6.

According to the second embodiment described above, since processing can be performed according to the operation state inside the lumen, of the medical apparatus, it is possible to assist endoscope-based examination by the operator.

Third Embodiment

Next, a third embodiment will be described. The third embodiment is different in terms of the arithmetic unit 7 of the image processing device 1 according to the first embodiment. In the following description, the configuration of an image processing device according to the third embodiment will be described first, and then, the process executed by an image processing device according to the third embodiment will be described. The same components as those of the image processing device 1 according to the first embodiment will be denoted by the same reference numerals and the description thereof will be omitted.

Configuration of Image Processing Device

Figure 13:
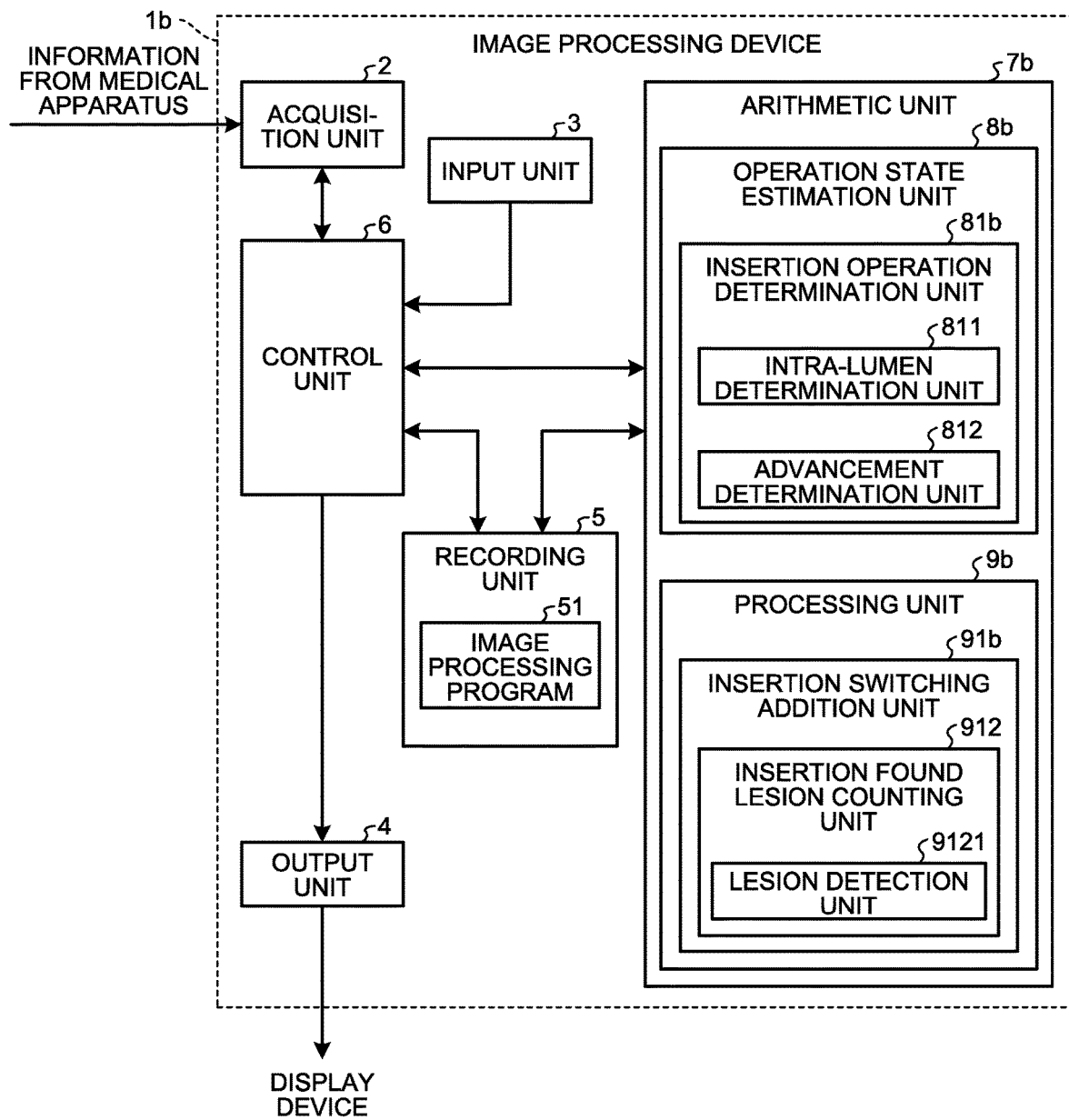
FIG. 13 is a block diagram illustrating a configuration of an image processing device according to a third embodiment.

FIG. 13 is a block diagram illustrating a configuration of an image processing device according to the third embodiment. An image processing device 1b illustrated in FIG. 13 includes an arithmetic unit 7b instead of the arithmetic unit 7 according to the first embodiment described above. The arithmetic unit 7b includes a processing unit 9b instead of the processing unit 9 according to the first embodiment described above. The processing unit 9b includes an insertion switching addition unit 91b instead of the insertion switching addition unit 91 according to the first embodiment described above.

The insertion switching addition unit 91b includes an insertion found lesion counting unit 912 that counts the number of target lesions during insertion of the medical apparatus. Moreover, the insertion found lesion counting unit 912 includes a lesion detection unit 9121 that detects a lesion from an intraluminal image.

Processing of Image Processing Device

Figure 14:
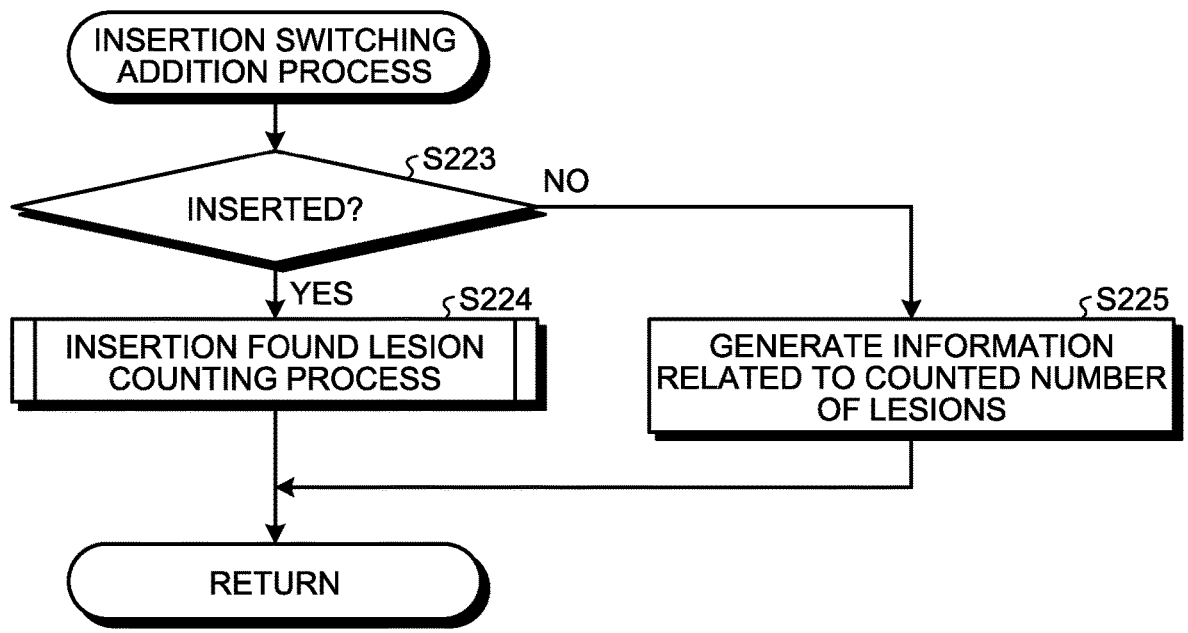
FIG. 14 is a flowchart illustrating an overview of a insertion switching addition process executed by the image processing device according to the third embodiment.

Next, the process executed by the image processing device 1b will be described. The image processing device 1b executes processing similar to that of the image processing device 1 according to the first embodiment and is different in terms of the insertion switching addition process in FIG. 7. In the following description, the insertion switching addition process executed by the image processing device 1b will be described. FIG. 14 is a flowchart illustrating an overview of the insertion switching addition process executed by the image processing device 1b.

As illustrated in FIG. 14, when an operation state estimation unit 8b estimates that the medical apparatus is inside the lumen (Step S223: Yes), the insertion found lesion counting unit 912 executes an insertion found lesion counting process of counting the number of target lesions (Step S224). After Step S224 is performed, the image processing device 1b returns to the subroutine of the switching addition process in FIG. 6.

Figure 15:
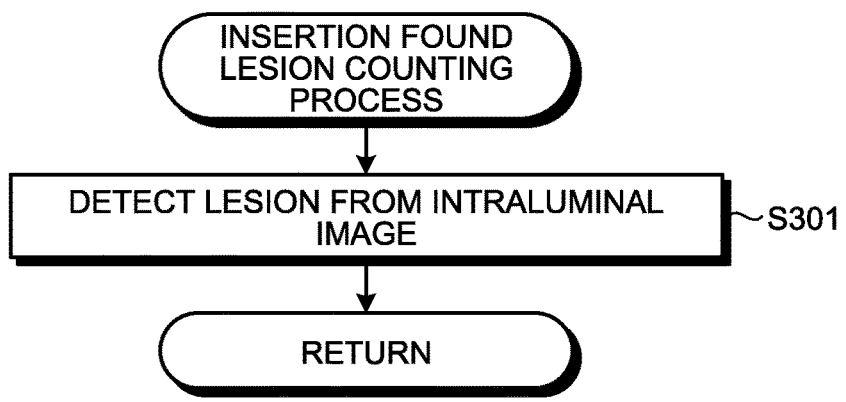
FIG. 15 is a flowchart illustrating an overview of an insertion found lesion counting process in FIG. 14.

FIG. 15 is a flowchart illustrating an overview of the insertion found lesion counting process of Step S224 in FIG. 14. As illustrated in FIG. 15, the lesion detection unit 9121 detects a lesion from an intraluminal image (Step S301). Specifically, the lesion detection unit 9121 counts the number of lesions found during insertion (counts the number of specific regions in which the degree of similarity to a reference is within a predetermined range) by performing well-known template matching or the like with respect to the intraluminal images sequentially input from the medical apparatus via the acquisition unit 2 using a predetermined reference. After Step S301 is performed, the image processing device 1b returns to the subroutine of the insertion switching addition process in FIG. 14.

Returning to FIG. 14, the description of the insertion switching addition process will be continued.

In Step S223, when the operation state estimation unit 8b estimates that the medical apparatus is not being inserted into the lumen (Step S223: No), the insertion switching addition unit 91b generates information related to the number of lesions counted by the insertion found lesion counting unit 912 and outputs the same to the output unit 4 (Step S225). After Step S225 is performed, the image processing device 1b returns to the subroutine of the switching addition process in FIG. 6.

According to the third embodiment described above, since processing can be performed according to the operation state inside the lumen, of the medical apparatus, it is possible to assist endoscope-based examination by the operator.

Fourth Embodiment

Next, a fourth embodiment will be described. The fourth embodiment is different in terms of the arithmetic unit 7b of the image processing device 1b according to the third embodiment. In the following description, the configuration of an image processing device according to the fourth embodiment will be described first, and then, the process executed by an image processing device according to the fourth embodiment will be described. The same components as those of the image processing device 1b according to the third embodiment will be denoted by the same reference numerals and the description thereof will be omitted. The same components as those of the image processing device 1b according to the second embodiment will be denoted by the same reference numerals and the description thereof will be omitted.

Configuration of Image Processing Device

Figure 16:
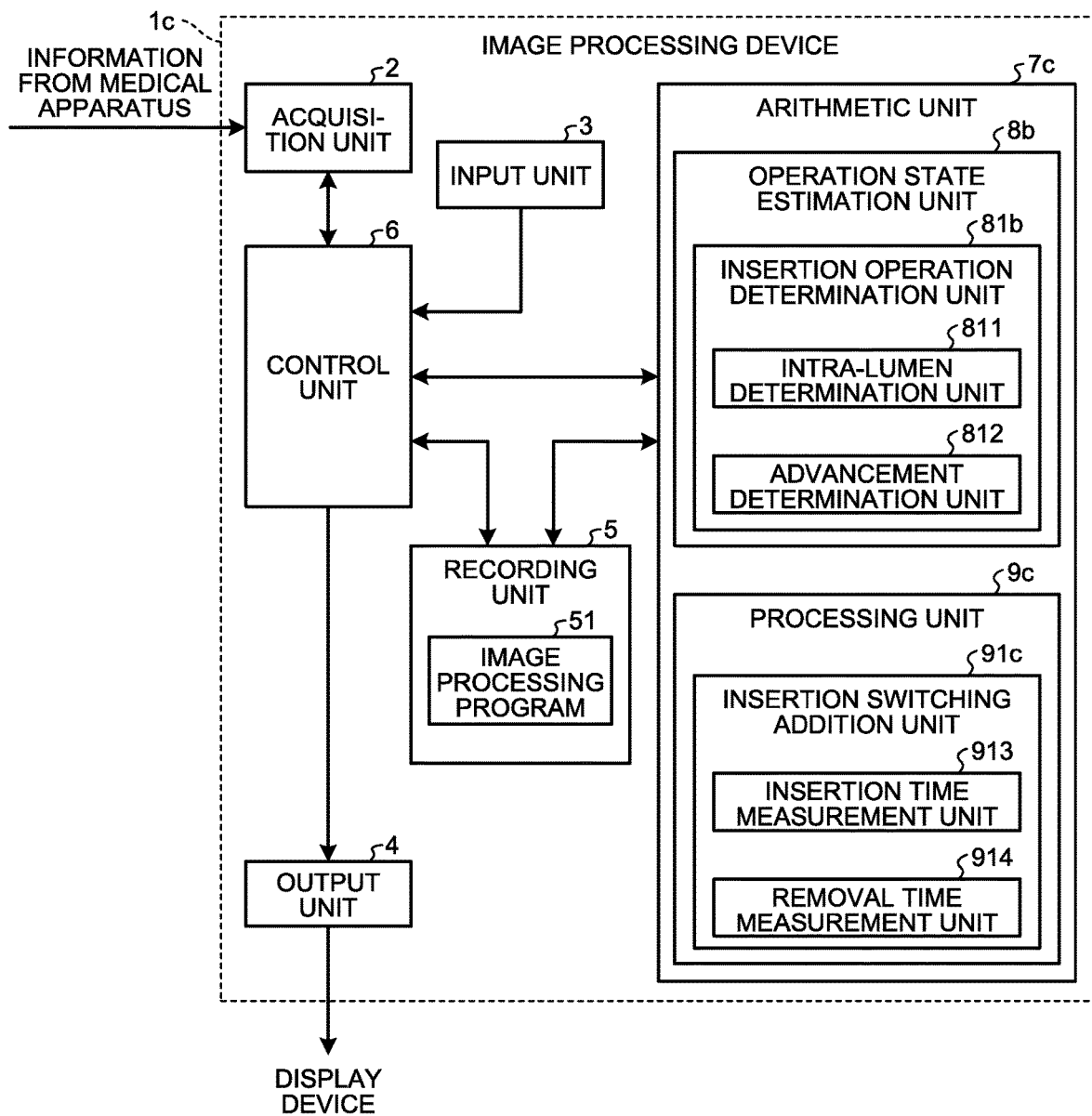
FIG. 16 is a block diagram illustrating a configuration of an image processing device according to a fourth embodiment.

FIG. 16 is a block diagram illustrating a configuration of an image processing device according to the fourth embodiment. An image processing device 1c illustrated in FIG. 16 includes an arithmetic unit 7c instead of the arithmetic unit 7b according to the third embodiment described above. The arithmetic unit 7c includes a processing unit 9c instead of the processing unit 9b according to the third embodiment described above. The processing unit 9c includes an insertion switching addition unit 91c instead of the insertion switching addition unit 91b according to the third embodiment described above.

The insertion switching addition unit 91c includes an insertion time measurement unit 913 that measures the time in which the medical apparatus is inserted into the lumen and a removal time measurement unit 914 that measures the time until the medical apparatus is removed from the deepest portion to be placed outside the lumen.

Processing of Image Processing Device

Next, the process executed by the image processing device 1c will be described. The image processing device 1c executes processing similar to that of the image processing device 1 according to the first embodiment and is different in terms of the insertion switching addition process in FIG. 7. In the following description, the insertion switching addition process executed by the image processing device 1c will be described.

Figure 17:
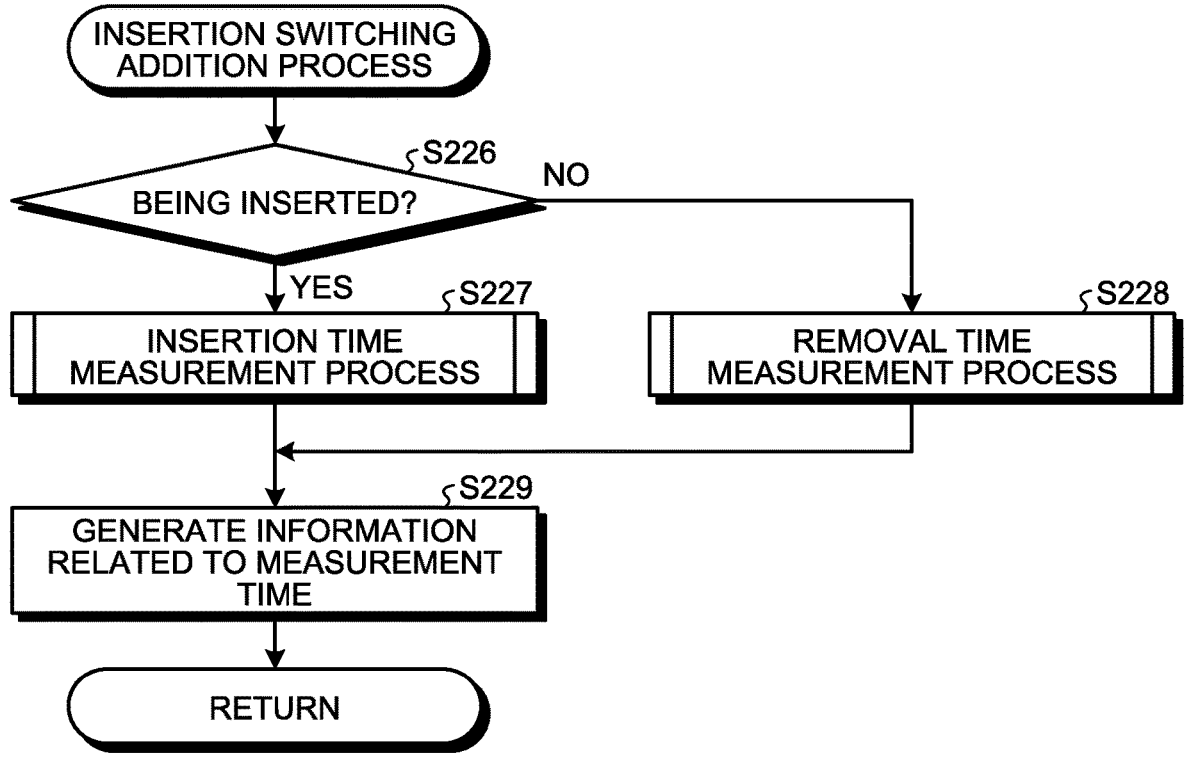
FIG. 17 is a flowchart illustrating an overview of a insertion switching addition process executed by the image processing device according to the fourth embodiment.

FIG. 17 is a flowchart illustrating an overview of the insertion switching addition process executed by the image processing device 1c. As illustrated in FIG. 17, first, when the operation state estimation unit 8b estimates that the medical apparatus is being inserted into the lumen (Step S226: Yes), the insertion time measurement unit 913 executes an insertion time measurement process of measuring the time in which the medical apparatus is inserted into the lumen (Step S227). After Step S227 is performed, the image processing device 1c proceeds to Step S229 to be described later.

Figure 18:
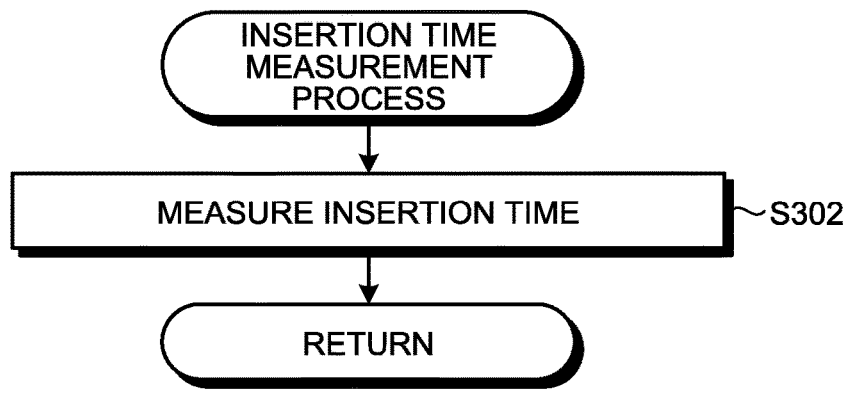
FIG. 18 is a flowchart illustrating an overview of an insertion time measurement process in FIG. 17.

FIG. 18 is a flowchart illustrating an overview of the insertion time measurement process of Step S227 in FIG. 17. As illustrated in FIG. 18, the insertion time measurement unit 913 starts measurement from a time point at which the intra-lumen determination unit 811 determines that the medical apparatus is inside the lumen and measures a period in which the advancement determination unit 812 determines that the medical apparatus is in the advancement as an insertion time (Step S302). After Step S302 is performed, the image processing device 1c returns to the subroutine of the insertion switching addition process in FIG. 17.

Returning to FIG. 17, the description of the insertion switching addition process will be continued.

In Step S226, when the operation state estimation unit 8b estimates that the medical apparatus is not being inserted into the lumen (Step S226: No), the removal time measurement unit 914 executes a removal time measurement process of measuring the time in which the medical apparatus is removed from the lumen (Step S228). After Step S228 is performed, the image processing device 1c proceeds to Step S229 to be described later.

Figure 19:
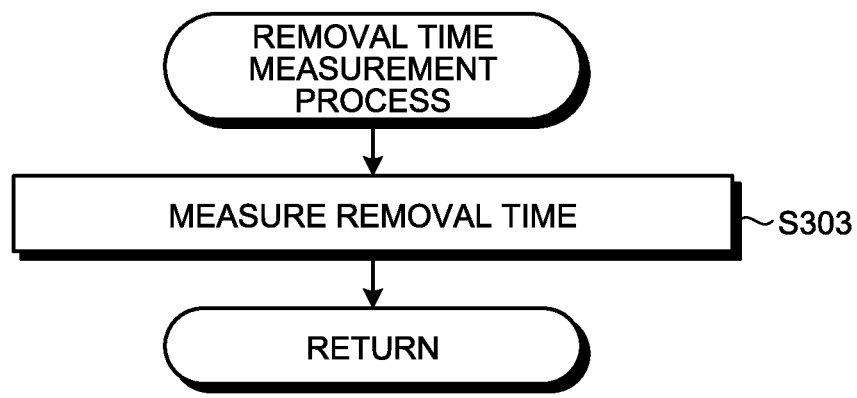
FIG. 19 is a flowchart illustrating an overview of a removal time measurement process in FIG. 17.

FIG. 19 is a flowchart illustrating an overview of the removal time measurement process of Step S228 in FIG. 17. As illustrated in FIG. 19, the removal time measurement unit 914 starts measurement from a time point at which the advancement determination unit 812 determines that the image is the deepest portion and measures a period in which the medical apparatus is removed out of the lumen of the subject as a removal time (Step S303). After Step S303 is performed, the image processing device 1c returns to the subroutine of the insertion switching addition process in FIG. 17.

Returning to FIG. 17, the description of Step S229 and the subsequent steps will be continued.

In Step S229, the insertion switching addition unit 91c generates information related to the measurement time of the insertion time or the removal time and outputs the same to the output unit 4. Here, the insertion switching addition unit 91c may allow the output unit 4 to output the insertion time or the removal time as a report or the like. Moreover, the insertion switching addition unit 91c may estimate the reliability or the difficulty of the examination based on the insertion time and the removal time. In this case, when the removal time is extremely shorter than a predetermined time (for example, the removal time is shorter than six minutes which is set as an index in general examination), the insertion switching addition unit 91c may estimate that the reliability of the examination of an operator is low and the output unit 4 may output the reliability to a display device. Moreover, when the insertion time is extremely longer than a predetermined time, the insertion switching addition unit 91c may estimate the difficulty of the examination of an operator is high, for example, and the output unit 4 may output the difficulty to a display device. After Step S229, the image processing device 1c returns to the subroutine of the switching addition process in FIG. 6.

According to the fourth embodiment described above, since processing can be performed according to the operation state inside the lumen, of the medical apparatus, it is possible to assist endoscope-based examination by the operator.

In the fourth embodiment, although the insertion time and the removal time are output, the insertion time and the removal time may be recorded on the recording unit 5, for example, and after examination on a subject ends, the output unit 4 may output the insertion time and the removal time to a diagnosis report created by the user.

In the fourth embodiment, the reliability or the difficulty of the examination that a user has conducted on a subject may be determined based on the insertion time and the removal time.

Fifth Embodiment

Next, a fifth embodiment will be described. The fifth embodiment is different in terms of the arithmetic unit 7b of the image processing device 1b according to the third embodiment. In the following description, the configuration of an image processing device according to the fifth embodiment will be described first, and then, the process executed by an image processing device according to the fifth embodiment will be described. The same components as those of the image processing device 1b according to the third embodiment will be denoted by the same reference numerals and the description thereof will be omitted.

Configuration of Image Processing Device

Figure 20:
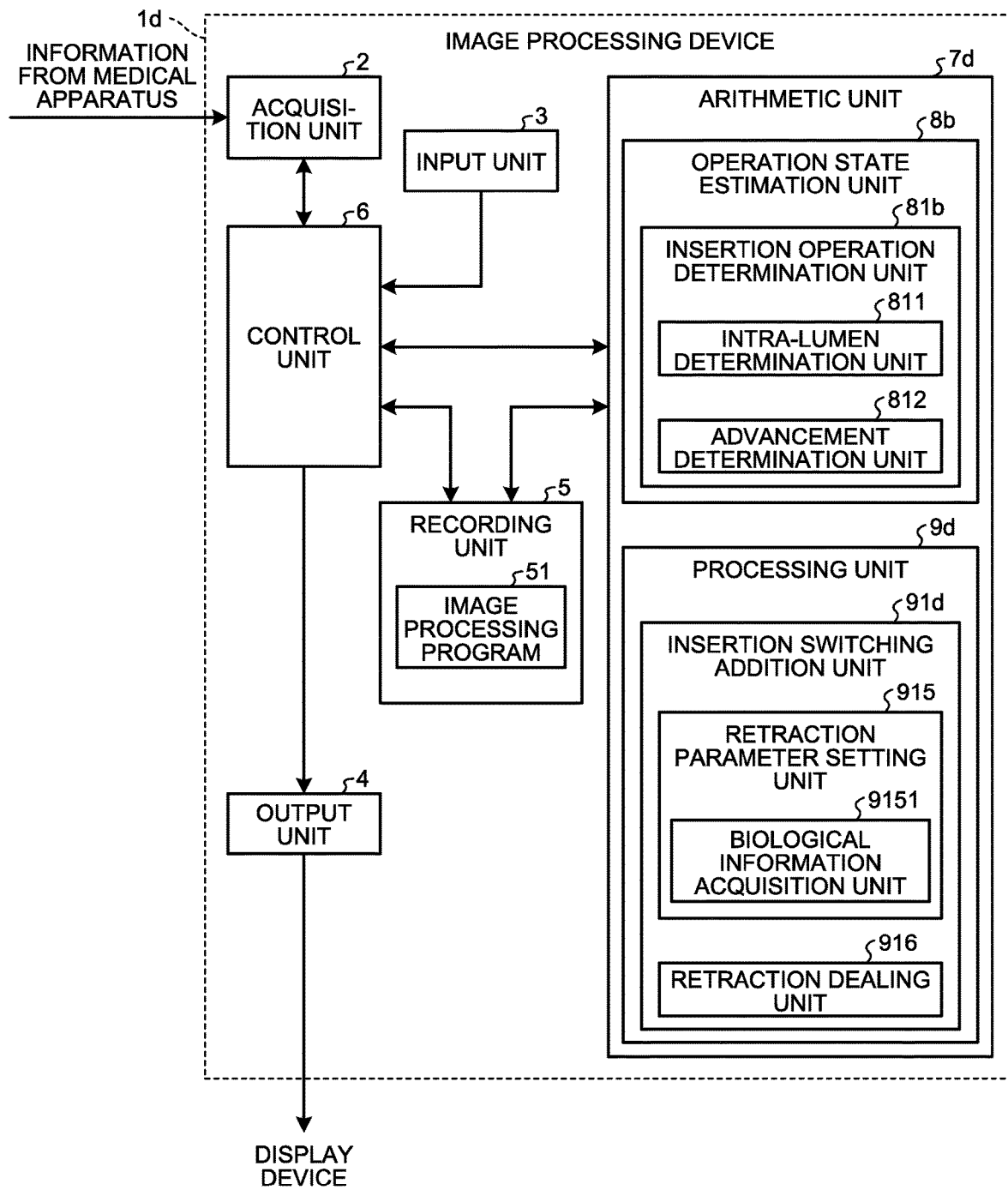
FIG. 20 is a block diagram illustrating a configuration of an image processing device according to a fifth embodiment.

FIG. 20 is a block diagram illustrating a configuration of an image processing device according to the fifth embodiment. An image processing device 1d illustrated in FIG. 20 includes an arithmetic unit 7d instead of the arithmetic unit 7b according to the third embodiment described above. The arithmetic unit 7d includes a processing unit 9d instead of the processing unit 9b according to the third embodiment described above. The processing unit 9d includes an insertion switching addition unit 91d instead of the insertion switching addition unit 91b according to the third embodiment described above.

The insertion switching addition unit 91d includes a retraction parameter setting unit 915 that acquires parameters necessary for supporting the retraction of the medical apparatus and a retraction dealing unit 916 that deals with the retraction of the medical apparatus in the lumen. Moreover, the retraction parameter setting unit 915 includes a biological information acquisition unit 9151 that acquires information related to a living body based on the intraluminal image.

Processing of Image Processing Device

Next, the process executed by the image processing device 1d will be described. The image processing device 1d executes processing similar to that of the image processing device 1 according to the first embodiment and is different in terms of the insertion switching addition process in FIG. 7. In the following description, the insertion switching addition process executed by the image processing device 1d will be described.

Figure 21:
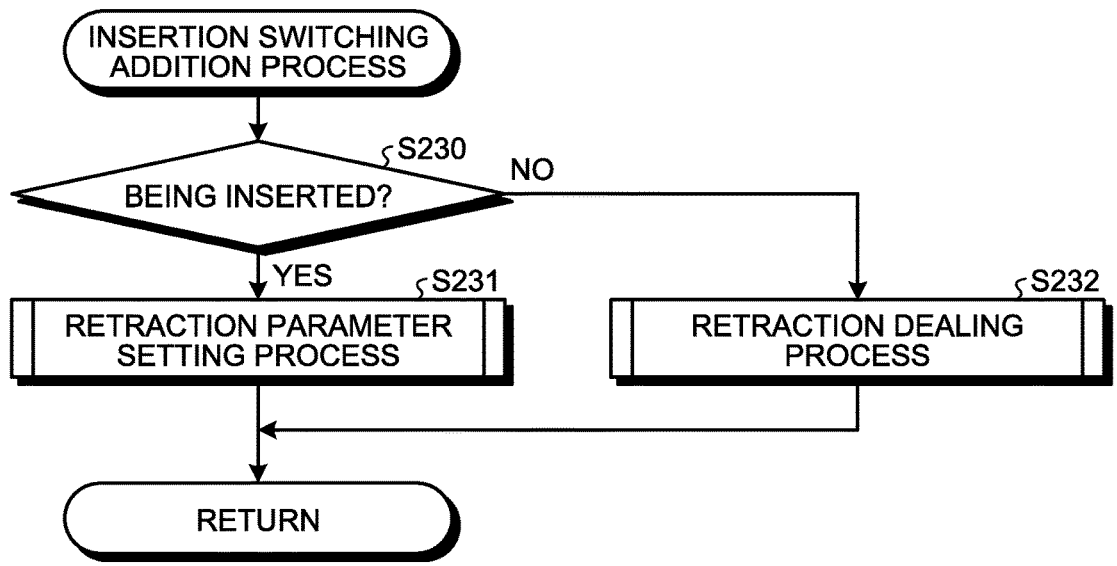
FIG. 21 is a flowchart illustrating an overview of a insertion switching addition process executed by the image processing device according to the fifth embodiment.

FIG. 21 is a flowchart illustrating an overview of the insertion switching addition process executed by the image processing device 1d. As illustrated in FIG. 21, first, when the operation state estimation unit 8b estimates that the medical apparatus is being inserted into the lumen (Step S230: Yes), the retraction parameter setting unit 915 executes a retraction parameter setting process of acquiring parameters necessary for dealing the retraction of the medical apparatus (Step S231). After Step S231 is performed, the image processing device 1d returns to the subroutine of the switching addition process in FIG. 6.

Figure 22:
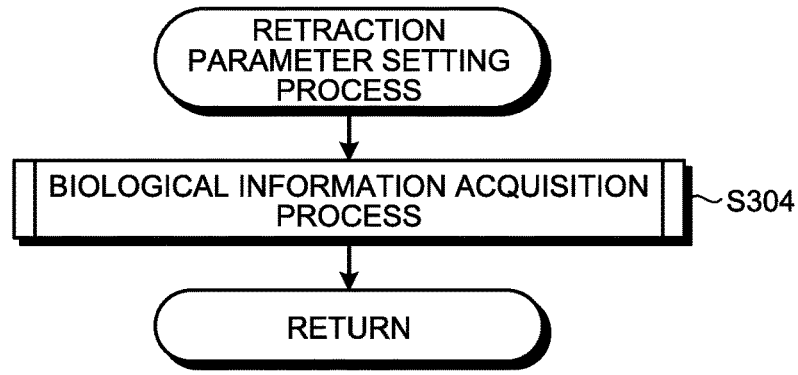
FIG. 22 is a flowchart illustrating an overview of a retraction parameter setting process in FIG. 21.

FIG. 22 is a flowchart illustrating an overview of the retraction parameter setting process of Step S231 in FIG. 21. As illustrated in FIG. 22, the biological information acquisition unit 9151 executes a biological information acquisition process of acquiring information related to a living body based on the intraluminal image acquired by the acquisition unit 2 (Step S304). After Step S304 is performed, the image processing device 1d returns to the subroutine of the insertion switching addition process in FIG. 21.

Figure 23:
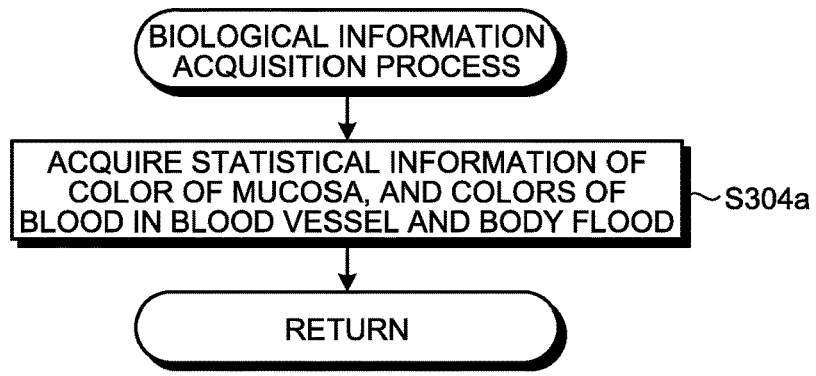
FIG. 23 is a flowchart illustrating an overview of a biological information acquisition process in FIG. 22.

FIG. 23 is a flowchart illustrating an overview of the biological information acquisition process of Step S304 in FIG. 22. As illustrated in FIG. 23, the biological information acquisition unit 9151 acquires statistical information such as the color of a mucosa, and the colors of the blood in a blood vessel and body fluid based on the intraluminal image (Step S304a). Specifically, the biological information acquisition unit 9151 acquires the biological information which is likely to change depending on a subject, such as a mucosa, a blood vessel, body fluid, and dregs from the intraluminal image using a well-known technology based on the RGB image forming operation of the intraluminal image. After Step S304a is performed, the image processing device 1d returns to the subroutine of the retraction parameter setting process in FIG. 22.

Returning to FIG. 21, the description of the insertion switching addition process will be continued.

In Step S230, when the operation state estimation unit 8b estimates that the medical apparatus is not being inserted into the lumen (Step S230: No), the retraction dealing unit 916 executes a retraction dealing process of dealing with the retraction of the medical apparatus (Step S232). After Step S232 is performed, the image processing device 1d returns to the subroutine of the switching addition process in FIG. 6.

Figure 24:
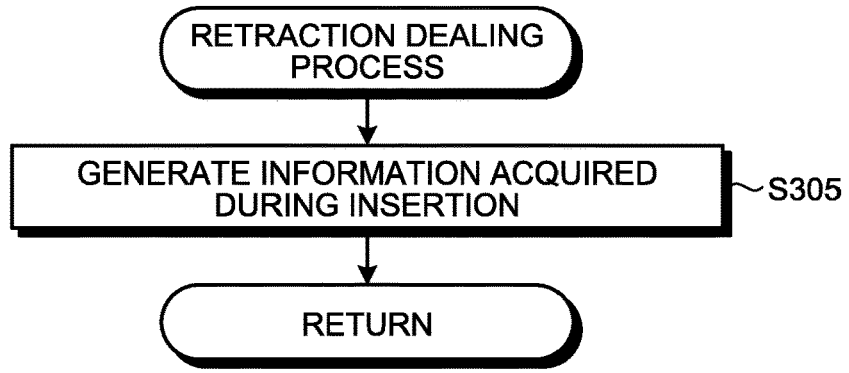
FIG. 24 is a flowchart illustrating an overview of a retraction dealing process in FIG. 21.

FIG. 24 is a flowchart illustrating an overview of the retraction dealing process of Step S232 in FIG. 21. As illustrated in FIG. 24, the retraction dealing unit 916 generates information related to the biological information acquired by the retraction parameter setting unit 915 when the medical apparatus is in the advancement inside the lumen and outputs the same to the output unit 4 (Step S305). Specifically, the retraction dealing unit 916 generates information related to the position of a lesion candidate (a specific region) and the position of a difficult advancing portion included in the biological information acquired by the biological information acquisition unit 9151 during removal of the medical apparatus. Alternatively, the retraction dealing unit 916 performs an operation of setting parameters for image processing uniquely suitable for a subject to the medical apparatus when the medical apparatus is removed from the deepest portion based on the biological information acquired by the biological information acquisition unit 9151. In this way, it is easy to detect lesions or the like in the retraction. After Step S305 is performed, the image processing device 1d returns to the subroutine of the insertion switching addition process in FIG. 21.

According to the fifth embodiment described above, since processing can be performed according to the operation state inside the lumen, of the medical apparatus, it is possible to assist endoscope-based examination by the operator.

First Modification of Fifth Embodiment

Next, a first modification of the fifth embodiment will be described. The first modification of the fifth embodiment is different in terms of the biological information acquisition process executed by the image processing device. In the following description, a biological information acquisition process executed by an image processing device according to the first embodiment of the fifth embodiment will be described. The same components as those of the image processing device 1b according to the third embodiment will be denoted by the same reference numerals and the description thereof will be omitted.

Figure 25:
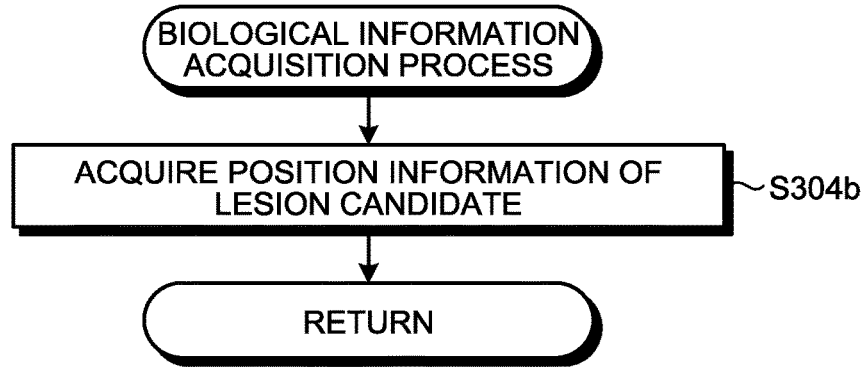
FIG. 25 is a flowchart illustrating an overview of a biological information acquisition process executed by an image processing device according to a first modification of the fifth embodiment.

FIG. 25 is a flowchart illustrating an overview of the biological information acquisition process executed by the image processing device according to the first modification of the fifth embodiment. As illustrated in FIG. 25, the biological information acquisition unit 9151 acquires the position information of a lesion candidate based on the intraluminal image (Step S304b). Specifically, the biological information acquisition unit 9151 creates a reference for detecting a lesion candidate (a specific region) in advance, identifies a lesion candidate by performing well-known pattern matching with respect to the intraluminal images sequentially input from the medical apparatus via the acquisition unit 2, and acquires the lesion candidate (the specific region) and the position information by acquiring the information related to the position of the imaging device from the medical apparatus via the acquisition unit 2 and acquiring the position of the imaging device based on the intraluminal images sequentially input from the medical apparatus. Here, the acquired position information of the lesion candidate is displayed on a display device by the processing unit 9d outputting the position information to the output unit 4 when the advancement determination unit 812 determines that the medical apparatus is in the retraction in the middle of being removed from the lumen. Naturally, the processing unit 9d may calculate the movement amount associated with removal of the medical apparatus based on the detection result from sensors of the medical apparatus and may cause the output unit 4 to output the position information of the lesion candidate acquired by the biological information acquisition unit 9151 to the display device based on the calculation result when the medical apparatus has approached the vicinity of the position of the lesion candidate. After Step S304b is performed, the image processing device 1d returns to the subroutine of the retraction parameter setting process in FIG. 22.

According to the first modification of the fifth embodiment described above, since processing can be performed according to the operation state inside the lumen, of the medical apparatus, it is possible to assist endoscope-based examination by the operator.

Second Modification of Fifth Embodiment

Next, a second modification of the fifth embodiment will be described. The second modification of the fifth embodiment is different in terms of the biological information acquisition process executed by the image processing device. In the following description, a biological information acquisition process executed by an image processing device according to the second modification of the fifth embodiment will be described. The same components as those of the image processing device 1b according to the third embodiment will be denoted by the same reference numerals and the description thereof will be omitted.

Figure 26:
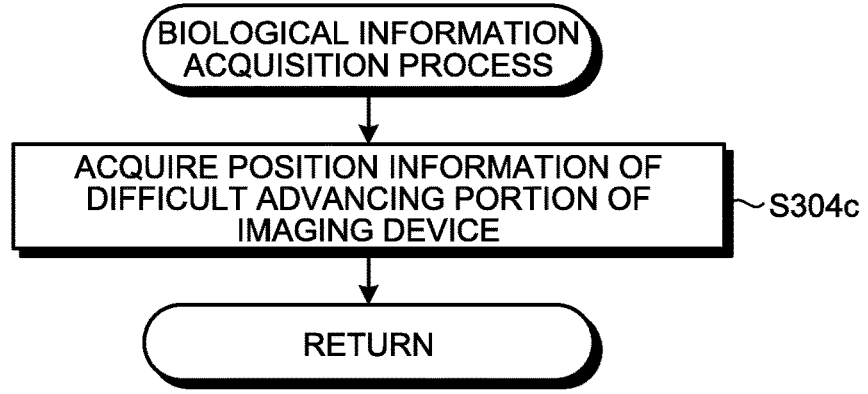
FIG. 26 is a flowchart illustrating an overview of a biological information acquisition process executed by an image processing device according to a second modification of the fifth embodiment.

FIG. 26 is a flowchart illustrating an overview of the biological information acquisition process executed by the image processing device according to the second modification of the fifth embodiment. As illustrated in FIG. 26, the biological information acquisition unit 9151 acquires the position information of a difficult advancing portion of the medical apparatus based on the intraluminal image (Step S304c). Specifically, the biological information acquisition unit 9151 calculates the movement of the distal end of the imaging device from an optical flow based on the intraluminal images successive in time and acquires the present position of the imaging device from the medical apparatus as the difficult advancing portion when the movement amount in the advancing direction is equal to the measurement result analysis device in the retracting direction (a removal direction) or when the movement amount in the advancing direction is larger than the movement amount in the retracting direction. Moreover, the biological information acquisition unit 9151 acquires the present position of the imaging device from the medical apparatus as the difficult advancing portion based on the information from the medical apparatus and the information from sensors such as an acceleration sensor and a motion sensor provided at the distal end of the imaging device when there is a small change in the position of the medical apparatus inside the lumen or when the medical apparatus repeats advancing and retracting. Moreover, the processing unit 9d may cause the output unit 4 to output the position information of the difficult advancing portion of the medical apparatus acquired by the biological information acquisition unit 9151 to the display device when the advancement determination unit 812 determines that the medical apparatus is in the retraction in the middle of being removed from the lumen. Naturally, the processing unit 9d may calculate the movement amount associated with removal of the medical apparatus based on the detection result from sensors of the medical apparatus and may cause the output unit 4 to output the position information of the difficult advancing portion of the medical apparatus acquired by the biological information acquisition unit 9151 to the display device based on the calculation result when the medical apparatus has approached the vicinity of the difficult advancing portion. After Step S304c is performed, the image processing device 1d returns to the subroutine of the retraction parameter setting process in FIG. 22.

According to the second modification of the fifth embodiment described above, since processing can be performed according to the operation state inside the lumen, of the medical apparatus, it is possible to assist endoscope-based examination by the operator.

Third Modification of Fifth Embodiment

Next, a third modification of the fifth embodiment will be described. The third modification of the fifth embodiment is different in terms of the arithmetic unit 7d of the fifth embodiment. In the following description, the configuration of an image processing device according to the third modification of the fifth embodiment will be described first, and then, the process executed by an image processing device according to the third modification of the fifth embodiment will be described. The same components as those of the image processing device 1d according to the fifth embodiment will be denoted by the same reference numerals and the description thereof will be omitted.

Configuration of Image Processing Device

Figure 27:
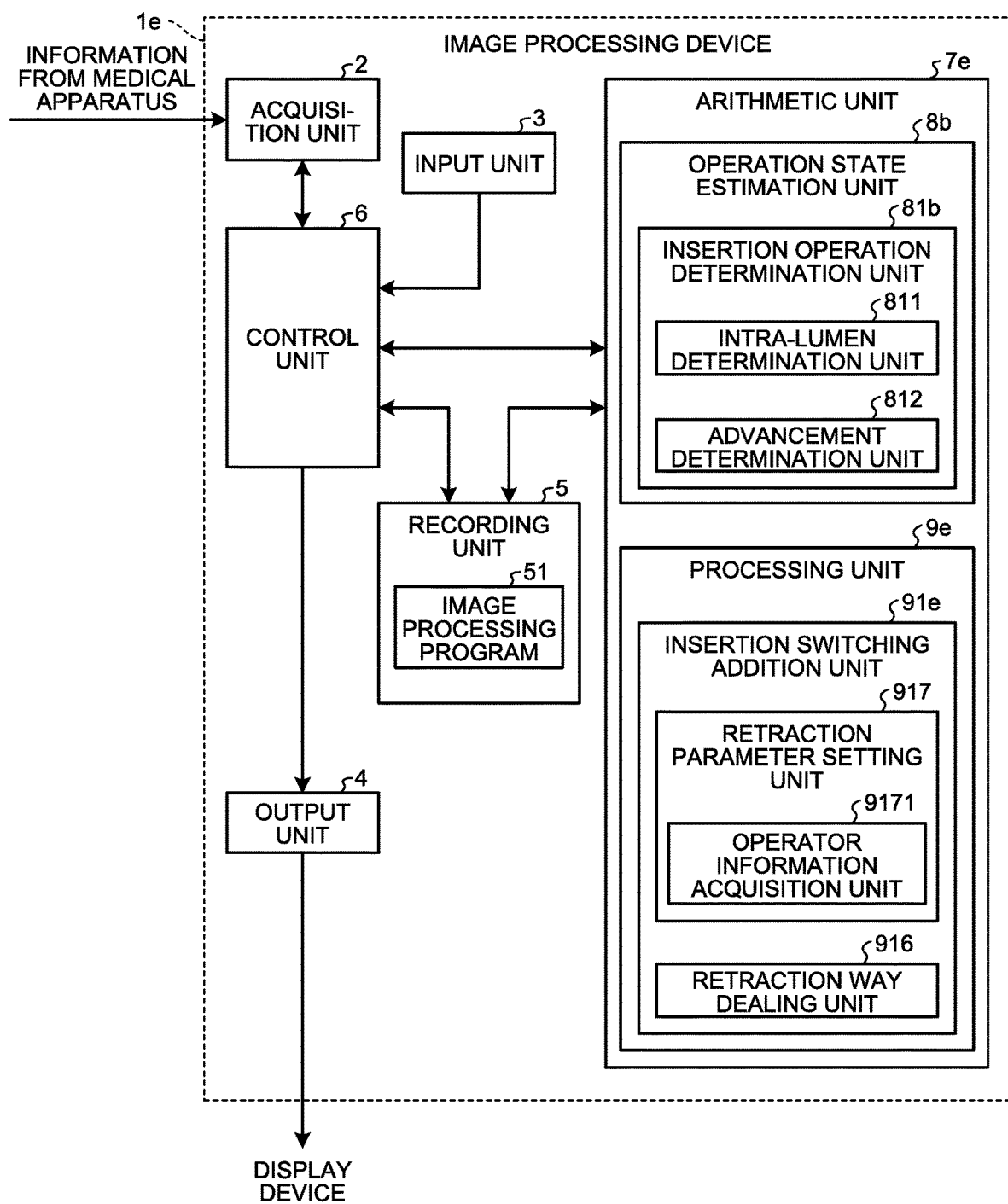
FIG. 27 is a block diagram illustrating a configuration of an image processing device according to a third modification of the fifth embodiment.

FIG. 27 is a block diagram illustrating a configuration of an image processing device according to the third modification of the fifth embodiment. An image processing device 1e illustrated in FIG. 27 includes an arithmetic unit 7e instead of the arithmetic unit 7d according to the fifth embodiment described above. The arithmetic unit 7e includes a processing unit 9e instead of the processing unit 9d according to the fifth embodiment described above. The processing unit 9e includes an insertion switching addition unit 91e instead of the insertion switching addition unit 91d according to the fifth embodiment described above.

The insertion switching addition unit 91a includes a retraction dealing unit 916 and a retraction parameter setting unit 917 that acquires parameters necessary for supporting the retraction of the medical apparatus. Moreover, the retraction parameter setting unit 917 includes an operator information acquisition unit 9171 that acquires information on an operator of the medical apparatus.

Processing of Image Processing Device

Next, the process executed by the image processing device 1e will be described. The image processing device 1e executes processing similar to that of the image processing device 1d according to the fifth embodiment and is different in terms of the retraction parameter setting process in FIG. 22. In the following description, the retraction parameter setting process executed by the image processing device 1e will be described.

Figure 28:
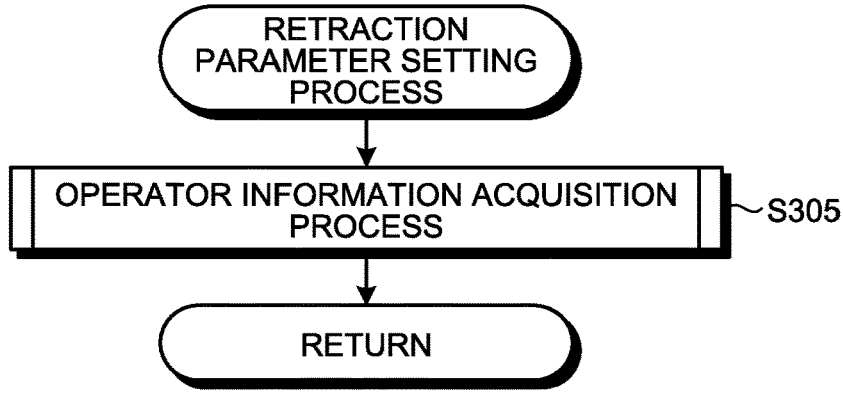
FIG. 28 is a flowchart illustrating an overview of a retraction parameter setting process executed by the image processing device according to a third modification of the fifth embodiment.

FIG. 28 is a flowchart illustrating an overview of the retraction parameter setting process executed by the image processing device 1e. As illustrated in FIG. 28, the operator information acquisition unit 9171 executes an operator information acquisition process of acquiring the information on an operator of the medical apparatus (Step S305). After Step S305 is performed, the image processing device 1e returns to the subroutine of the switching addition process in FIG. 6.

Figure 29:
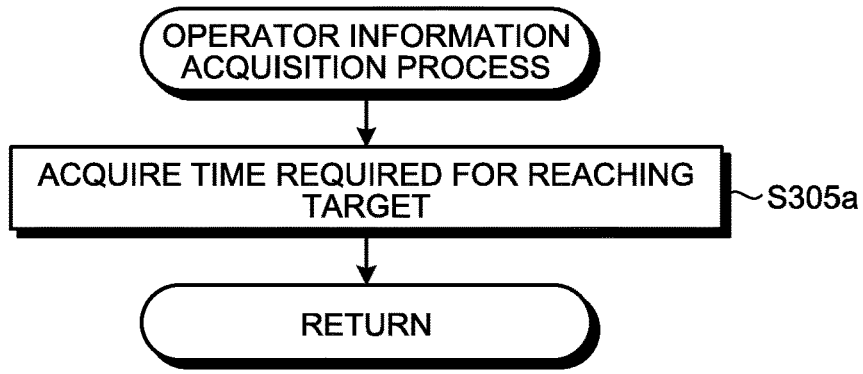
FIG. 29 is a flowchart illustrating an overview of an operator information acquisition process in FIG. 28.

FIG. 29 is a flowchart illustrating an overview of the operator information acquisition process of Step S305 in FIG. 28. As illustrated in FIG. 29, the operator information acquisition unit 9171 acquires the time required for the imaging device included in the medical apparatus reaches the target deepest portion (Step S305a). Specifically, the operator information acquisition unit 9171 acquires the time elapsed after the imaging device included in the medical apparatus is inserted into the lumen until the imaging device reaches the deepest portion using a determination method similar to that used by the advancement determination unit 812 described in Step S122 of FIG. 9. Here, the reason why the time is acquired is to measure the difficulty of advancing, to measure the capability of the operation level of the operator, and to support the retraction. In this way, when the insertion time is long, it can be determined that the shape of an organ of a patient who is a subject is complex or the operation level of the operator is low. After Step S305a is performed, the image processing device 1e returns to the subroutine of the retraction parameter setting process in FIG. 28.

According to the third modification of the fifth embodiment described above, since processing can be performed according to the operation state inside the lumen, of the medical apparatus, it is possible to assist endoscope-based examination by the operator.

Fourth Modification of Fifth Embodiment

Next, a fourth modification of the fifth embodiment will be described. The fourth modification of the fifth embodiment is different in terms of the operator information acquisition process executed by the image processing device. In the following description, the operator information acquisition process executed by the image processing device according to the fourth modification of the fifth embodiment will be described. The same components as those of the image processing device 1e according to the third modification of the fifth embodiment will be denoted by the same reference numerals and the description thereof will be omitted.

Figure 30:
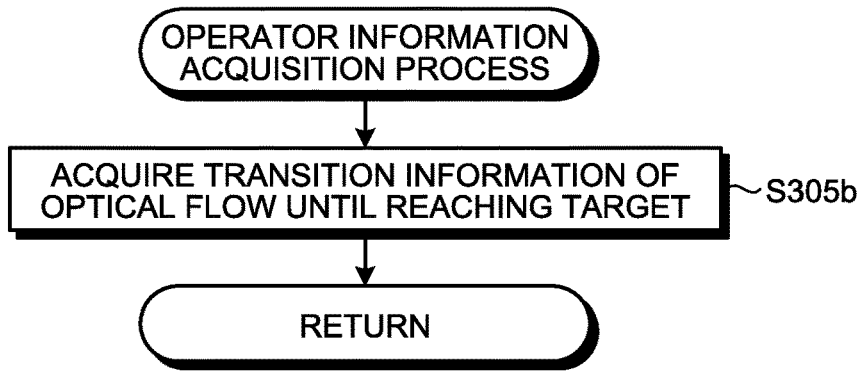
FIG. 30 is a flowchart illustrating an overview of an operator information acquisition process executed by an image processing device according to a fourth modification of the fifth embodiment.

FIG. 30 is a flowchart illustrating an overview of the biological information acquisition process executed by the image processing device according to the fourth modification of the fifth embodiment. As illustrated in FIG. 30, the operator information acquisition unit 9171 acquires the transition information of the optical flow until the imaging device included in the medical apparatus reaches a target from the medical apparatus (Step S305b). Here, the reason why the transition information of the optical flow is acquired is to measure the difficulty of advancing, to measure the capability of the operation level of the operator, and to support the retraction. In this way, when the insertion time is long, it can be determined that the shape of an organ of a patient who is a subject is complex or the operation level of the operator is low. After Step S305b is performed, the image processing device 1e returns to the subroutine of the retraction parameter setting process in FIG. 28.

According to the fourth modification of the fifth embodiment described above, since processing can be performed according to the operation state inside the lumen, of the medical apparatus, it is possible to assist endoscope-based examination by the operator.

Sixth Embodiment

Next, a sixth embodiment will be described. The sixth embodiment is different in terms of the arithmetic unit 7b of the image processing device 1b according to the third embodiment. In the following description, the configuration of an image processing device according to the sixth embodiment will be described first, and then, the process executed by an image processing device according to the sixth embodiment will be described. The same components as those of the image processing device 1b according to the third embodiment will be denoted by the same reference numerals and the description thereof will be omitted.

Configuration of Image Processing Device

Figure 31:
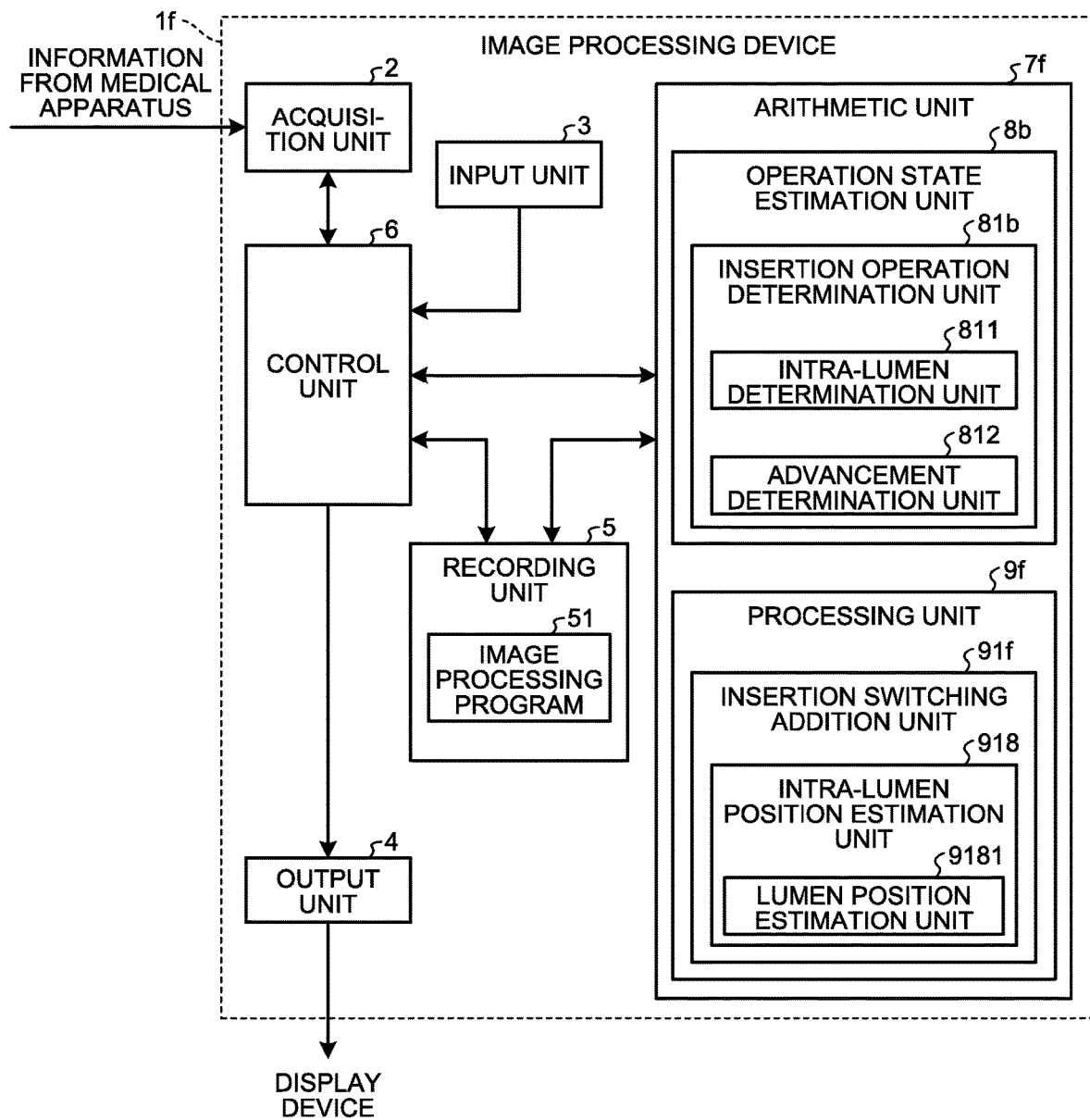
FIG. 31 is a block diagram illustrating a configuration of an image processing device according to the sixth embodiment.

FIG. 31 is a block diagram illustrating a configuration of an image processing device according to the sixth embodiment. An image processing device if illustrated in FIG. 31 includes an arithmetic unit 7f instead of the arithmetic unit 7b of the image processing device 1b according to the third embodiment described above. The arithmetic unit 7f includes a processing unit 9f instead of the processing unit 9b according to the third embodiment described above. The processing unit 9f includes an insertion switching addition unit 91f instead of the insertion switching addition unit 91b according to the third embodiment described above.

The insertion switching addition unit 91f estimates the lumen position and an organ being imaged by the imaging device based on the information from the medical apparatus when the imaging device included in the medical apparatus is inserted into the lumen. the insertion switching addition unit 91f includes an intra-lumen position estimation unit 918 that estimates the intra-lumen position imaged by the imaging device based on the intraluminal image. Moreover, the intra-lumen position estimation unit 918 includes a lumen position estimation unit 9181 that estimates the position of the lumen imaged by the imaging device.

Processing of Image Processing Device

Next, the process executed by the image processing device if will be described. The image processing device if executes processing similar to that of the image processing device 1 according to the first embodiment and is different in terms of the insertion switching addition process in FIG. 7. In the following description, the insertion switching addition process executed by the image processing device if will be described.

Figure 32:
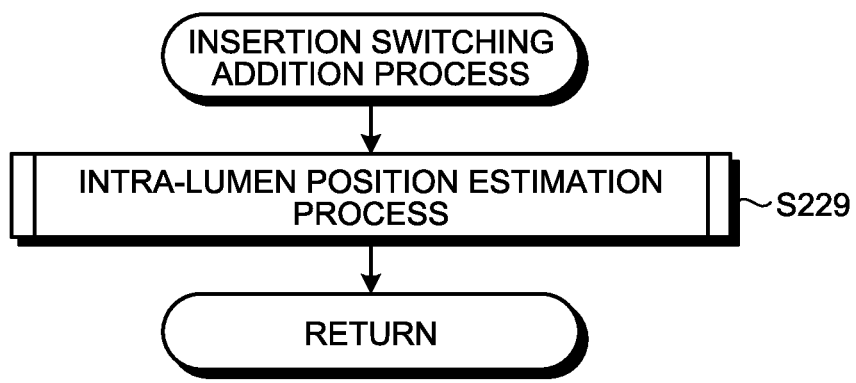
FIG. 32 is a flowchart illustrating an overview of a insertion switching addition process executed by the image processing device according to the sixth embodiment.

FIG. 32 is a flowchart illustrating an overview of the insertion switching addition process executed by the image processing device 1f. First, as illustrated in FIG. 32, the intra-lumen position estimation unit 918 executes an intra-lumen position estimation process of estimating the intra-lumen position imaged by the imaging device based on the intraluminal image and the estimation result of the operation state estimation unit 8b (Step S229). After Step S229, the image processing device 1f returns to the subroutine of the switching addition process in FIG. 6.

Figure 33:
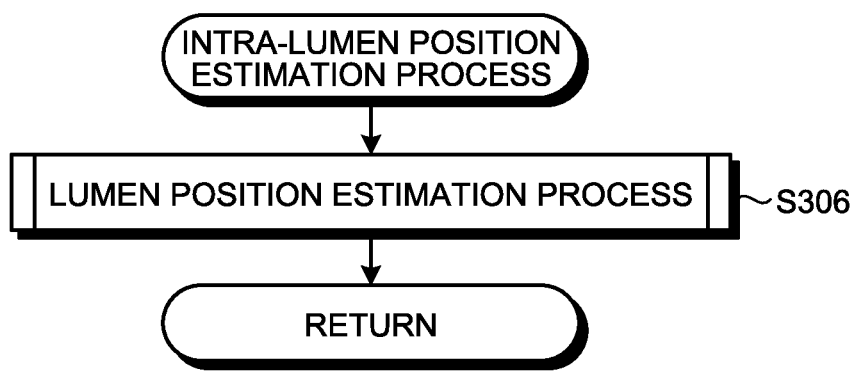
FIG. 33 is a flowchart illustrating an overview of an intra-lumen position estimation process in FIG. 32.

FIG. 33 is a flowchart illustrating an overview of the intra-lumen position estimation process of Step S229 in FIG. 32. As illustrated in FIG. 33, the lumen position estimation unit 9181 executes the lumen position estimation process of estimating the lumen position imaged by the imaging device based on the intraluminal image and the information from the sensors of the imaging device included in the medical apparatus (Step S306). After Step S306 is performed, the image processing device 1f returns to the subroutine of the insertion switching addition process in FIG. 32.

Figure 34:
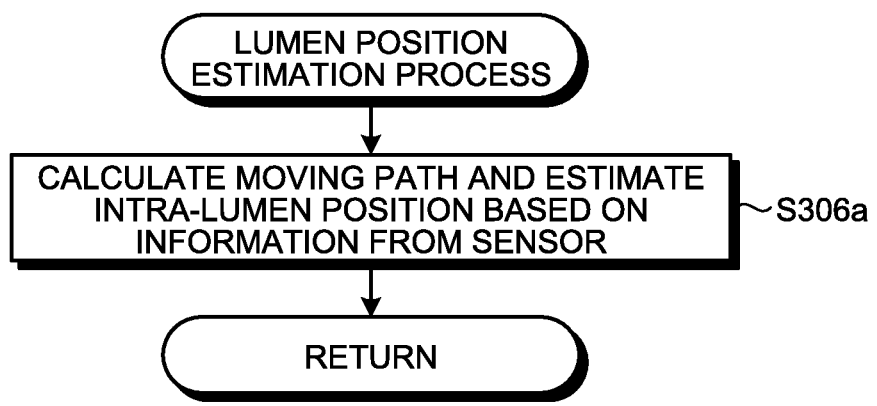
FIG. 34 is a flowchart illustrating an overview of a lumen position estimation process in FIG. 33.

FIG. 34 is a flowchart illustrating an overview of the lumen position estimation process of Step S306 in FIG. 33. As illustrated in FIG. 34, the lumen position estimation unit 9181 acquires information from the sensors of the imaging device included in the medical apparatus, calculates a moving path based on the acquired information, and estimates the intra-lumen position of the imaging device (Step S306a). In this case, the lumen position estimation unit 9181 may acquire an operation history of the operator on an operating unit included in the medical apparatus and estimate the intra-lumen position of the imaging device. In this way, it is possible to increase the estimation accuracy of the intra-lumen of the imaging device. After Step S306a is performed, the image processing device if returns to the subroutine of the intra-lumen position estimation process in FIG. 33.

According to the sixth embodiment described above, since processing can be performed according to the operation state inside the lumen, of the medical apparatus, it is possible to assist endoscope-based examination by the operator.

First Modification of Sixth Embodiment

Next, a first modification of the sixth embodiment will be described. The first modification of the sixth embodiment will be described. The first modification of the sixth embodiment is different in terms of the lumen position estimation process executed by the image processing device. In the following description, the lumen position estimation process executed by the image processing device according to the first modification of the sixth embodiment will be described. The same components as those of the image processing device if according to the sixth embodiment will be denoted by the same reference numerals and the description thereof will be omitted.

Figure 35:
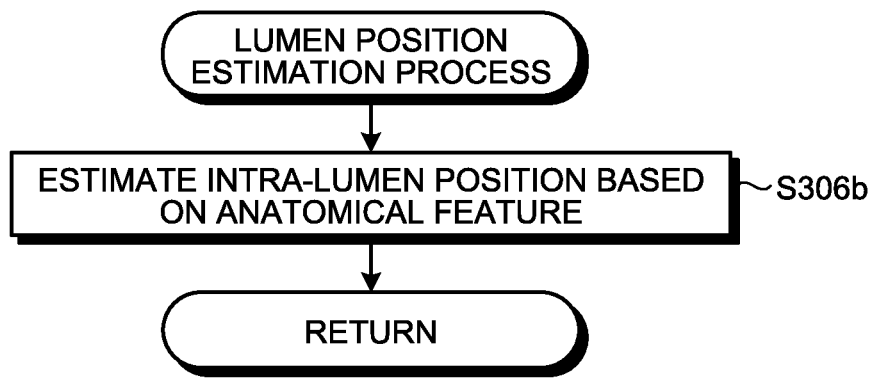
FIG. 35 is a flowchart illustrating an overview of a lumen position estimation process executed by an image processing device according to a first modification of the sixth embodiment.

FIG. 35 is a flowchart illustrating an overview of a lumen position estimation process executed by an image processing device according to the first modification of the sixth embodiment.

As illustrated in FIG. 35, the lumen position estimation unit 9181 estimates the intra-lumen position of the imaging device included in the medical apparatus based on an anatomical feature of the intraluminal image (Step S306b). Specifically, the lumen position estimation unit 9181 estimates the intra-lumen position of the imaging device included in the medical apparatus by comparing the intraluminal image with a predetermined reference indicating the anatomical difference of the lumen. After Step S306b is performed, the image processing device if returns to the subroutine of the intra-lumen position estimation process in FIG. 33.

According to the first modification of the sixth embodiment described above, since processing can be performed according to the operation state inside the lumen, of the medical apparatus, it is possible to assist endoscope-based examination by the operator.

Second Modification of Sixth Embodiment

Next, a second modification of the sixth embodiment will be described. The second modification of the sixth embodiment is different in terms of the configuration of the image processing device according to the sixth embodiment. In the following description, the configuration of an image processing device according to the second modification of the sixth embodiment will be described first, and then, the process executed by the image processing device according to the second modification of the sixth embodiment will be described. The same components as those of the image processing device if according to the sixth embodiment will be denoted by the same reference numerals and the description thereof will be omitted.

Figure 36:
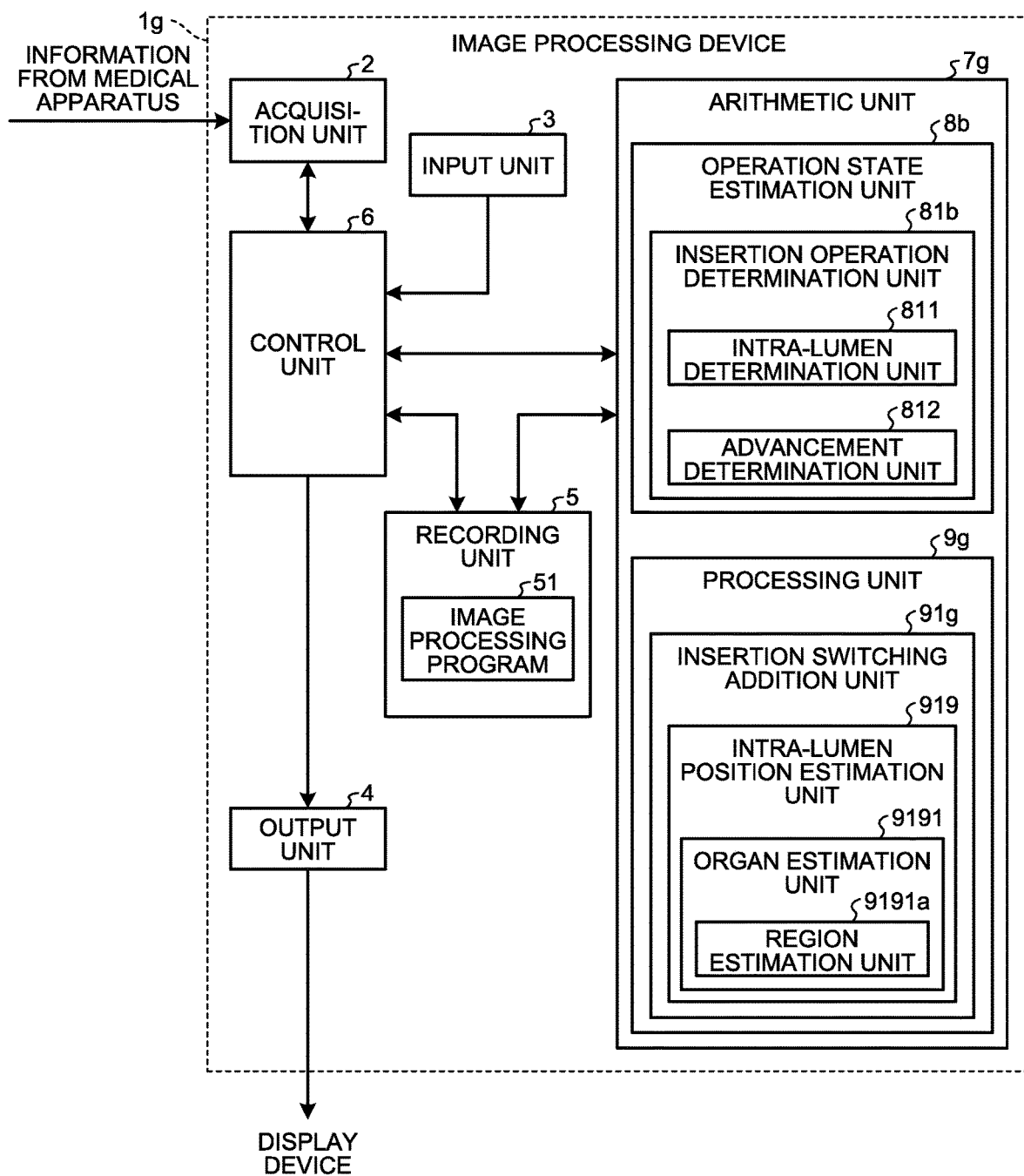
FIG. 36 is a block diagram illustrating a configuration of an image processing device according to a second modification of the sixth embodiment.

FIG. 36 is a block diagram illustrating a configuration of an image processing device according to the second modification of the sixth embodiment. An image processing device 1g illustrated in FIG. 36 includes an arithmetic unit 7g instead of the arithmetic unit 7f of the image processing device if according to the sixth embodiment. The arithmetic unit 7g includes a processing unit 9g instead of the processing unit 9f according to the sixth embodiment. The processing unit 9g includes an insertion switching addition unit 91g instead of the insertion switching addition unit 91f according to the sixth embodiment.

The insertion switching addition unit 91g estimates an organ imaged by the imaging device when the imaging device included in the medical apparatus is inserted into the lumen based on the information from the medical apparatus. The insertion switching addition unit 91g includes an intra-lumen position estimation unit 919 that estimates an organ or an intra-lumen position of the medical apparatus inside the lumen based on the intraluminal image. The intra-lumen position estimation unit 919 estimates the intra-lumen position imaged by the imaging device based on the intraluminal image. The intra-lumen position estimation unit 919 includes an organ estimation unit 9191 that estimates an organ imaged by the imaging device based on the intraluminal image. Moreover, the organ estimation unit 9191 includes a region estimation unit 919a that estimates the region of an organ imaged by the imaging device based on the intraluminal image.

Processing of Image Processing Device

Next, the process executed by the image processing device 1g will be described. The image processing device 1g executes processing similar to that of the image processing device 1 according to the first embodiment and is different in terms of the insertion switching addition process in FIG. 7. In the following description, the insertion switching addition process executed by the image processing device 1g will be described.

Figure 37:
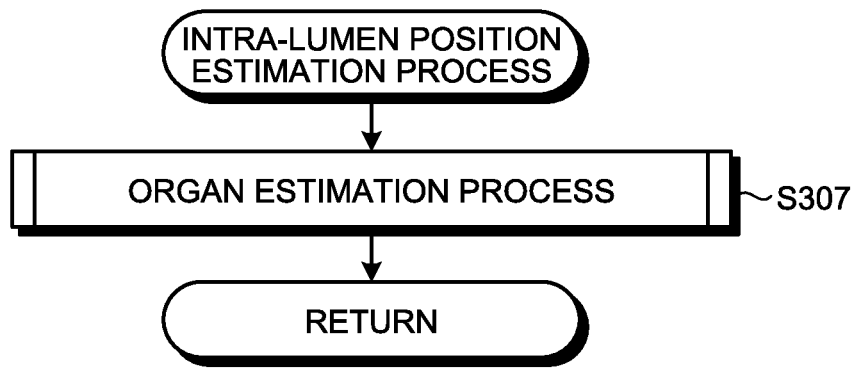
FIG. 37 is a flowchart illustrating an overview of an intra-lumen position estimation process executed by the image processing device according to a second modification of the sixth embodiment.

FIG. 37 is a flowchart illustrating an overview of the intra-lumen position estimation process executed by the image processing device 1g. As illustrated in FIG. 37, first, the organ estimation unit 9191 executes an organ estimation process of estimating an organ imaged by the imaging device based on the intraluminal image (Step S307). After Step S307 is performed, the image processing device 1g returns to the subroutine of the switching addition process in FIG. 6.

Figure 38:
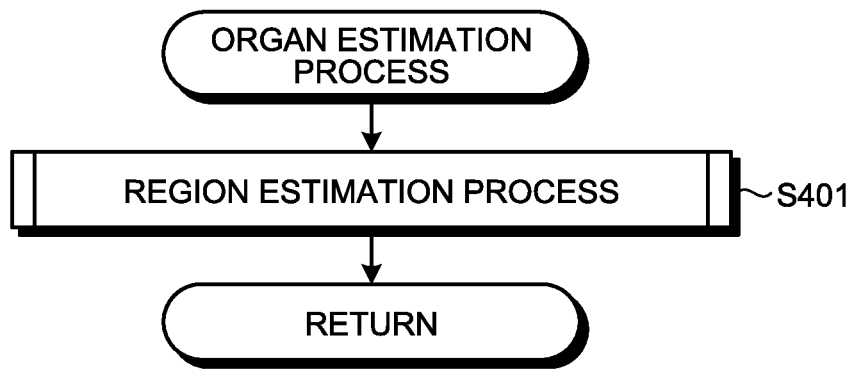
FIG. 38 is a flowchart illustrating an overview of an organ estimation process in FIG. 37.

FIG. 38 is a flowchart illustrating an overview of the organ estimation process of Step S307 in FIG. 37. As illustrated in FIG. 37, the region estimation unit 919a executes a region estimation process of estimating the region of an organ imaged by the imaging device based on the intraluminal image (Step S401). After Step S401 is performed, the image processing device 1g returns to the subroutine of the organ estimation process in FIG. 37.

Figure 39:
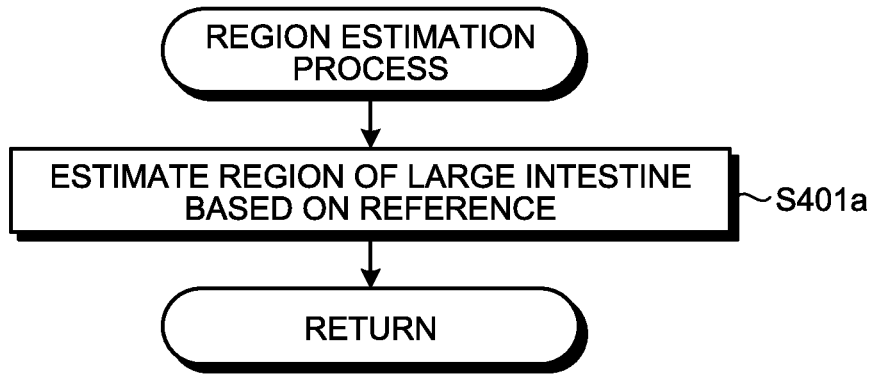
FIG. 39 is a flowchart illustrating an overview of a region estimation process in FIG. 38.

FIG. 39 is a flowchart illustrating an overview of the region estimation process in FIG. 38. As illustrated in FIG. 39, the region estimation unit 919a estimates the region of the large intestine captured in the intraluminal image based on a predetermined reference (Step S401a). Specifically, the region estimation unit 919a estimates the region of the large intestine by comparing the intraluminal image with a plurality of predetermined references for identifying the rectum, the sigmoid colon, the descending colon, the hepatic flexure, the transverse colon, the splenic flexure, the ascending colon, and the ileocecum. After Step S401a is performed, the image processing device 1g returns to the subroutine of the region estimation process in FIG. 38.

According to the second modification of the sixth embodiment described above, since processing can be performed according to the operation state inside the lumen, of the medical apparatus, it is possible to assist endoscope-based examination by the operator.

Figure 40:
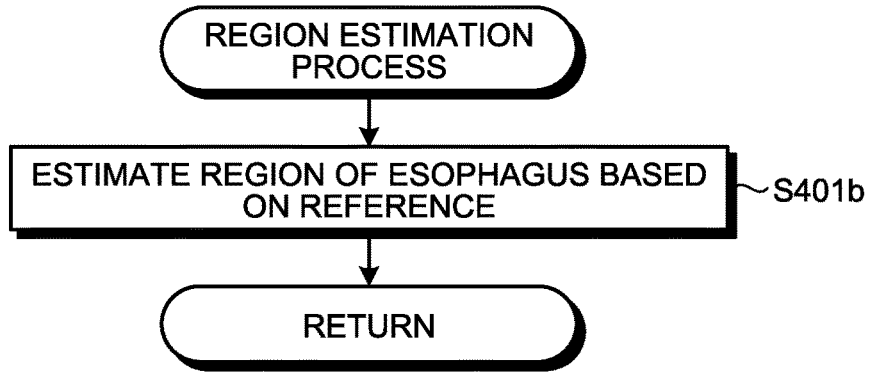
FIG. 40 is a flowchart illustrating an overview of another region estimation process executed by the image processing device according to a second modification of the sixth embodiment.

In the second modification of the sixth embodiment, although the region estimation unit 919a estimates the region of the large intestine as the region of an organ, the region of another organ may be estimated. FIG. 40 is a flowchart illustrating an overview of another region estimation process executed by the image processing device 1g.

As illustrated in FIG. 40, the region estimation unit 919a estimates the region of the esophagus captured in the intraluminal image based on a predetermined reference (Step S401b). Specifically, the region estimation unit 919a estimates the region of the esophagus by comparing the intraluminal image with a plurality of predetermined references for identifying the esophageal opening and the cardiac orifice. After Step S401b is performed, the image processing device 1g returns to the subroutine of the region estimation process in FIG. 38.

Figure 41:
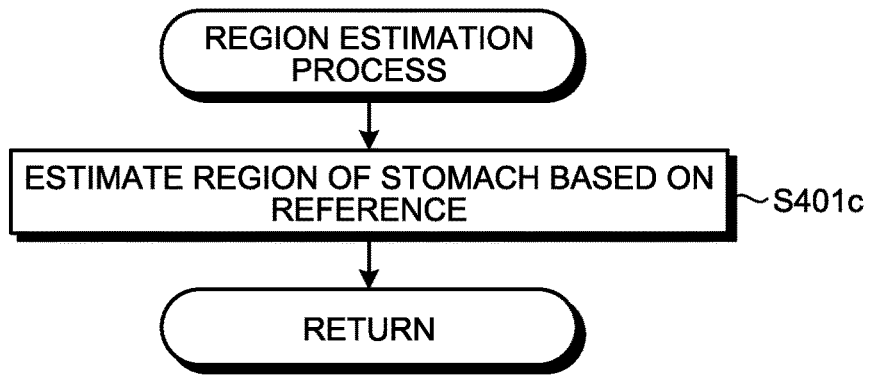
FIG. 41 is a flowchart illustrating an overview of another region estimation process executed by the image processing device according to a second modification of the sixth embodiment.

In the second modification of the sixth embodiment, the region of the stomach may be estimated as the region of an organ. FIG. 41 is a flowchart illustrating an overview of another region estimation process executed by the image processing device 1g. As illustrated in FIG. 41, the region estimation unit 919a estimates the region of the stomach captured in the intraluminal image based on a predetermined reference (Step S401c). Specifically, the region estimation unit 919a estimates the region of the stomach by comparing the intraluminal image with a plurality of predetermined references for identifying the gastric fundus, the gastric body, the pyloric zone, and the pylorus. After Step S401c is performed, the image processing device 1g returns to the subroutine of the region estimation process in FIG. 38.

Figure 42:
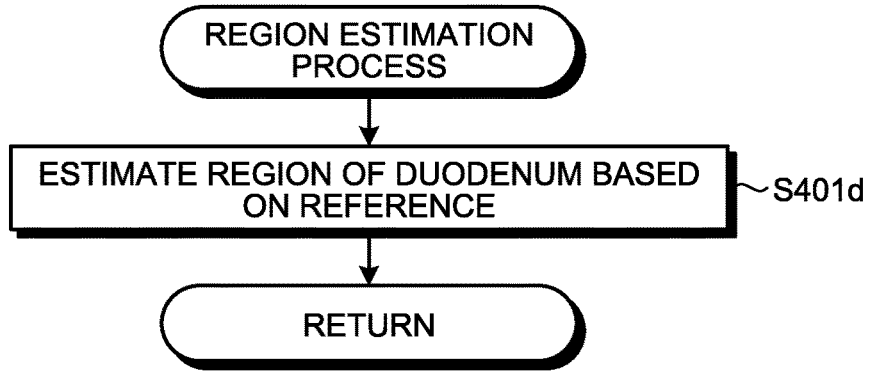
FIG. 42 is a flowchart illustrating an overview of another region estimation process executed by the image processing device according to a second modification of the sixth embodiment.

In the second modification of the sixth embodiment, the region of the duodenum may be estimated as the region of an organ. FIG. 42 is a flowchart illustrating an overview of another region estimation process executed by the image processing device 1g. As illustrated in FIG. 42, the region estimation unit 919a estimates the region of the duodenum captured in the intraluminal image based on a predetermined reference (Step S401d). Specifically, the region estimation unit 919a estimates the region of the duodenum by comparing the intraluminal image with a plurality of predetermined references for identifying the duodenal bulb and the papilla vater. After Step S401d is performed, the image processing device 1g returns to the subroutine of the region estimation process in FIG. 38.

Figure 43:
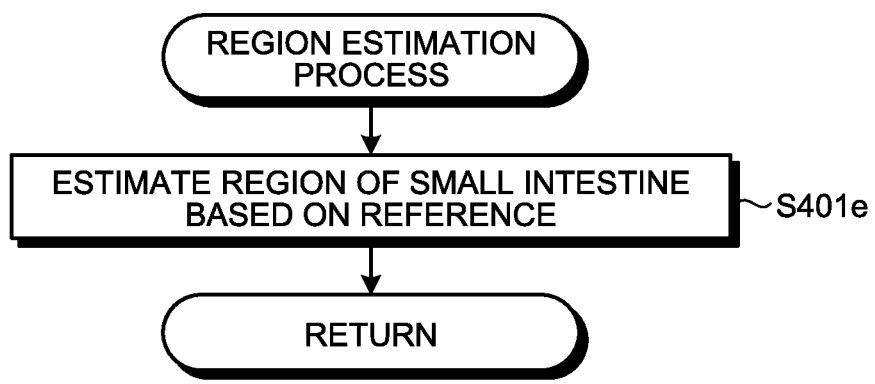
FIG. 43 is a flowchart illustrating an overview of another region estimation process executed by the image processing device according to a second modification of the sixth embodiment.

In the second modification of the sixth embodiment, the region of the small intestine may be estimated as the region of an organ. FIG. 43 is a flowchart illustrating an overview of another region estimation process executed by the image processing device 1g. As illustrated in FIG. 43, the region estimation unit 919a estimates the region of the small intestine captured in the intraluminal image based on a predetermined reference (Step S401e). Specifically, the region estimation unit 919a estimates the region of the small intestine by comparing the intraluminal image with a plurality of predetermined references for identifying the jejunum and the ileum. After Step S401e is performed, the image processing device 1g returns to the subroutine of the region estimation process in FIG. 38.

Other Embodiments

The present disclosure can be realized by a computer system such as a personal computer or a workstation executing an image processing program recorded on a recording device. Moreover, such a computer system may be used by connecting to another computer system or an apparatus such as a server via a public line such as a local area network (LAN), a wide area network (WAN), or the Internet. In this case, the image processing device according to the first to sixth embodiments and the modifications thereof may acquire image data of the intra-lumen image via these networks, output image processing results to various output apparatuses such as a viewer or a printer connected via these networks, and store the image processing results in a storage device (for example, a recording medium readable by a reader connected to a network) connected via these networks.

In the description of the flowcharts of the present specification, expressions such as "first," "after that," or "subsequently" are used to specify a sequential relationship between processes of steps. However, the sequence of processes necessary to implement the present disclosure is not uniquely determined by such expressions. That is, the sequence of the processes in the flowcharts described in the present specification may be changed as long as it is not contradictory.

The present disclosure is not limited to the first to sixth embodiments and the modifications thereof, but the plurality of components disclosed in the embodiments and the modifications may be combined appropriately to form variations. For example, the present disclosure may be formed by excluding some components from all components illustrated in the embodiments and the modifications and may be formed by appropriately combining the components illustrated in different embodiments and modifications.

According to the present disclosure, an advantage that processing can be performed according to an operation state in the lumen, of the medical apparatus is obtained.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
a processor configured to:
acquire a predetermined reference image of a turning back point where an endoscope changes a direction of travel from inserting to removing;
acquire a sequence of intraluminal images captured by an imaging device;
determine a degree of matching between each one of the sequence of intraluminal images and the predetermined reference image when each one of the sequence of intraluminal images is acquired, wherein determine the degree of matching comprises comparing each one of the sequence of intraluminal images with the predetermined reference image at pixel level when each one of the sequence of intraluminal images is acquired;
determine that the endoscope reached the turning back point when the degree of matching reached a predetermined reference value; and
output a signal for switching an operation state of the endoscope from an insertion state and a removal state in response to determining that the endoscope reached the turning back point.

2. The image processing device according to claim 1, wherein the processor is configured to:
determine an operation state of the imaging device is an inserting state that indicates the imaging device is inserted into a lumen based on the sequence of intraluminal images; and
in response to determining that the imaging device is inserted into the lumen, measure an insertion time period in which the imaging device is inserted into the lumen.

3. The image processing device according to claim 2, wherein the processor is configured to set, as the insertion time period, a period in which the endoscope is advancing from a time point when the endoscope is determined to be inserted into the lumen.

4. The image processing device according to claim 1, wherein the processor is configured to:
in response to determining that the degree of matching reached the predetermined reference value, control the imaging device to obtain an image.

5. The image processing device according to claim 1, wherein:
the processor is configured to acquire information necessary for a retracting operation; and
the retracting operation includes at least one of discovery, identification, and treatment of a specific region.

6. The image processing device according to claim 1, wherein the processor is configured to detect a target lesion based on the intraluminal images and count number of lesions.

7. The image processing device according to claim 1, wherein the processor is configured to, in response to determining that the endoscope reached the turning back point, perform at least one of: estimating a lumen position and identifying an organ imaged by the imaging device in the intraluminal images sequentially obtained.

8. The image processing device according to claim 7, wherein the processor is configured to estimate the lumen position based on the intraluminal images.

9. The image processing device according to claim 7, wherein the processor is configured to identify a region of an organ imaged by the imaging device in the intraluminal images sequentially obtained.

10. The image processing device according to claim 9, wherein:
when the organ is a large intestine, the processor is configured to identify the region of the large intestine as one of a rectum, a sigmoid colon, a descending colon, a hepatic flexure, a transverse colon, a transverse colon, a splenic flexure, an ascending colon, and an ileocecum;
when the organ is an esophagus, the processor is configured to identify the region of the esophagus as one of an esophageal opening and a cardiac orifice;
when the organ is a stomach, the processor is configured to identify the region of the stomach as one of a gastric fundus, a gastric body, a pyloric zone, and a pylorus;
when the organ is a duodenum, the processor is configured to identify the region of the duodenum as one of a duodenal bulb and a papilla vater; and
when the organ is a small intestine, the processor is configured to identify the region of the small intestine as one of a jejunum and an ileum.

11. The image processing device according to claim 1, wherein the processor is configured to:
control a display to display the operation state of the endoscope.

12. The image processing device according to claim 1, wherein:
the predetermined reference image is an image of an observation target in a lumen.

13. The image processing device according to claim 1, wherein: the insertion state and the removal state are operation states of the endoscope in a lumen.

14. The image processing device according to claim 13, wherein: the insertion state is the operation state until a distal end of the endoscope reaches a target position after the distal end enters into the lumen; the removal state is the operation state until the distal end of the endoscope comes out of the lumen after the distal end reaches the target position inside the lumen.

15. The image processing device according to claim 1, wherein under the insertion state, the endoscope advances towards an observation target that is an ileocecum.

16. A system comprising: the image processing device according to claim 1; and the endoscope comprising an insertion portion and the imaging device provided in the insertion portion.

17. A method for determining an operation state of an imaging device, the method comprising:
acquiring, by the processor, a predetermined reference image of a turning back point where an endoscope changes a direction of travel from inserting to removing;
acquiring a sequence of intraluminal images captured by the imaging device;
determining a degree of matching between each one of the sequence of intraluminal images and the predetermined reference image when each one of the sequence of intraluminal images is acquired, wherein determining the degree of matching comprises comparing each one of the sequence of intraluminal images with the predetermined reference image at pixel level when each one of the sequence of intraluminal images is acquired;
determining, by the processor, that the endoscope reached the turning back point when the degree of matching reached a predetermined reference value; and
outputting a signal for switching an operation state of the endoscope from an insertion state and a removal state in response to determining that the endoscope reached the turning back point.

18. A non-transitory computer readable recording medium on which an executable program is recorded, the executable program instructing a processor of an image processing device to determine an operation state of an imaging device by performing the steps of:
acquire a predetermined reference image of a turning back point where an endoscope changes a direction of travel from inserting to removing;
acquire a sequence of intraluminal images captured by the imaging device;
determine a degree of matching between each one of the sequence of intraluminal images and the predetermined reference image when each one of the sequence of intraluminal images is acquired, wherein determine the degree of matching comprises comparing each one of the sequence of intraluminal images with the predetermined reference image at pixel level when each one of the sequence of intraluminal images is acquired;
determine that the endoscope reached the turning back point when the degree of matching reached a predetermined reference value; and
output a signal for switching an operation state of the endoscope from an insertion state and a removal state in response to determining that the endoscope reached the turning back point.

* * * * *